United States Patent [19]
Lehar et al.

[11] Patent Number: 5,843,659
[45] Date of Patent: Dec. 1, 1998

[54] APOPTOSIS GENE EI24, COMPOSITIONS, AND METHODS OF USE

[75] Inventors: Sophie M. Lehar, Berlin; Braydon C. Guild, Concord, both of Mass.

[73] Assignee: Apoptosis Technology, Inc., Cambridge, Mass.

[21] Appl. No.: 619,362

[22] Filed: Mar. 21, 1996

[51] Int. Cl.[6] ............................. C12Q 1/68; C12P 21/00; C12N 5/10; C07H 21/04
[52] U.S. Cl. ............................. 435/6; 435/69.1; 435/914; 435/320.1; 435/325; 536/23.5
[58] Field of Search .............................. 435/6, 69.1, 91.4, 435/320.1, 325; 536/23.5

[56] References Cited

PUBLICATIONS

Friedlander et al. A mutant p53 that discriminates between p53–responsive genes cannot induce apoptosis. Mol and Cell. Biol. vol. 16(9):4961–4971, Sep. 1996.
Ludwig et al. Differential activation of target cellular promoters by p53 mutants with impaired apoptotic function. Mol and Cell. Biol. Vol. 16(9):4951–4960, Sep. 1996.

Primary Examiner—James Ketter
Assistant Examiner—William Sandals
Attorney, Agent, or Firm—Hale and Dorr LLP

[57] ABSTRACT

Disclosed is the isolation and characterization of EI24, a novel gene whose 2.4 kb mRNA is induced following etoposide treatment. Induction of EI24 mRNA by etoposide required expression of wild-type p53. Overexpression of functional p53 was sufficient to induce expression of the EI24 mRNA. The EI24 mRNA was also induced in a p53-dependent manner by ionizing irradiation of primary murine thymocytes. The invention is thus directed to an isolated EI24 protein, nucleotide sequences coding for and regulating expression of the protein, antibodies directed against the protein, and recombinant vectors and host cells containing the genetic sequences coding for and regulating the expression of the protein sequence. The invention is also directed to genomic DNA, cDNA, and RNA encoding the EI24 protein sequence and to corresponding antisense RNA sequences. Antibodies can be used to detect EI24 in biological specimens, including, for example, human tissue samples. The present invention is further directed to methods of treating degenerative disorders characterized in inappropriate cell proliferation or inappropriate cell death. The present invention is further directed to methods for diagnosing degenerative disorders characterized in inappropriate cell proliferation or inappropriate cell death, as well as methods for monitoring the progress of such degenerative disorders.

18 Claims, 9 Drawing Sheets

```
TGAACCCGGG ACGCGAAAGG CGGCAGGGGC AGGCCTGGCG GCGGCGCGCG    50

GGACTCAGGC TTTCCCCAGG CCCTCCATGA TGAATGGTTT GGGGGCACTT   100
                               M  V  W  G  H  F          (6)
CCCTCTAGCT GTATTTGATA GTCTGGGCAG TGGAGAGATG GCTGACAGTG   150
 P  L  A  V  F  D  S  L  G  S  G  E  M  A  D  S         (22)
TCAAAACCTT TCTGCAGGAC CTTGGCAGGG GAATCAAAGA CTCCATCTGG   200
V  K  T  F  L  Q  D  L  G  R  G  I  K  D  S  I  W       (39)
GGCATCTGTA CCATCTCAAA GCTAGATGCT CGGATCCACC AGAAGAGAGA   250
 G  I  C  T  I  S  K  L  D  A  R  I  Q  Q  K  R  E      (56)
GGAACAGCGT CGAAGAAGGG CAAGTAGCCT CTTGGCCCAG AGGAGACCCC   300
  E  Q  R  R  R  R  A  S  S  L  L  A  Q  R  R  P        (72)
AGAGTGTAGA GCGGAAGCAA GAGAGTGAAC CACGTATTGT TAGTAGAATT   350
Q  S  V  E  R  K  Q  E  S  E  P  R  I  V  S  R  I       (89)
TTCCAGTGTT GTGCTTGGAA TGGTGGAGTA TTCTGGTTCA GTCTCCTCTT   400
 F  Q  C  C  A  W  N  G  G  V  F  W  F  S  L  L  L     (106)
GTTTTATCGA GTGTTTATTC CTGTACTTCA GTCAGTAACA GCCCGGATTA   450
 F  Y  R  V  F  I  P  V  L  Q  S  V  T  A  R  I        (122)
TTGGAGATCC ATCACTTCAT GGAGATGTTT GGTCATGGCT GGAATTCTTC   500
I  G  D  P  S  L  H  G  D  V  W  S  W  L  E  F  F      (139)
CTCACATCAA TTTTCAGTGC TCTTTGGGTG CTCCCCCTGT TTGTGCTTAG   550
 L  T  S  I  F  S  A  L  W  V  L  P  L  F  V  L  S     (156)
CAAAGTTGTG AATGCCATTT GGTTCCAAGA TATAGCTGAC TTGGCATTTG   600
 K  V  V  N  A  I  W  F  Q  D  I  A  D  L  A  F        (172)
AAGTATCAGG GAGGAAACCT CATCCATTCC CCAGTGTCAG CAAAATAATT   650
 E  V  S  G  R  K  P  H  P  F  P  S  V  S  K  I  I     (189)
GCTGACATGC TCTTCAACCT TTTGCTACAG GCACTTTTCC TTATTCAGGG   700
 A  D  M  L  F  N  L  L  L  Q  A  L  F  L  L  Q  G     (206)
GATGTTTGTG AGTCTCTTCC CCATCCATCT TGTGGGTCAG CTGGTTAGTC   750
  M  F  V  S  L  F  P  I  H  L  V  G  Q  L  V  S       (222)
TGCTGCATAT GTCTCTTCTC TATTCACTGT ACTGCTTTGA GTACCGTTGG   800
 L  L  H  M  S  L  L  Y  S  L  Y  C  F  E  Y  R  W     (239)
TTCAACAAAG GAATTGAAAT GCACCAGCGA TTGTCGAACA TAGAAAGGAA   850
 F  N  K  G  I  E  M  H  Q  R  L  S  N  I  E  R  N     (256)
TTGGCCTTAC TACTTTGGGT TTGGCTTGCC TTGGCTTTCC TCACAGCAAT   900
  W  P  Y  Y  F  G  F  G  L  P  W  L  S  Q  Q          (272)
GCAATCCTCC TACATTATCA GTGGCTGCCT CTTTTCTATC CTGTTTCCTT   950
 C  N  P  P  T  L  S  V  A  A  S  F  L  S  C  F  L     (289)
TATTCATCAT CAGCGCCAAT GAAGCAAAGA CTCCTGGAAA AGCATATCTT  1000
 Y  S  S  S  A  P  M  K  Q  R  L  L  E  K  H  I  F     (306)
TTCCAGTTGC GCCTATTCTC CTTGGTGGTC TTTTTAAGCA ACAGACTTTT  1050
 S  S  C  A  Y  S  P  W  W  S  F ***                    (317)
                                        [SEQ ID NO:8]
```

FIG.2A

```
CCACAAGACC GTCTACCTGC AGTCAGCCCT GAGCAGCTCG TCCTCTGCAG   1100
AGAAATTCCC TTCGCCACAT CCTTCTCCGG CCAAACTGAA AGCTGCTGCA   1150
GGCCATTGAG CCCTGCTGTC AAAGGGGTGG GTGGGACTGG GTGGAGGATG   1200
TGGCAGCTCT TTTCTCTGTT TTCCTCCCCC TGCCGTGGAA GGCAGAACCC   1250
ACTGCCAAGG GCCCTCTGCA TAGTCCCTTG TCTTTGAATT GGAATCTTCC   1300
TGACTCCAGT ATATGGATTT TTACCACCAC CCTAGGTCTG TAAGGACCAG   1350
TTTTCCAGCT GTTTTTTTAG CACTTGCCAG CTCCTGTGCC TGGACTGATT   1400
GATTTGAGTA CTTTTTTTCC CCTTTCCTTG TGTCATTTAC CCTCCCACTT   1450
CCTCCTGCCT TCCAGCACCC CTGGATGAAT GGGCTTTGTA ATTTTAACTG   1500
TTGTATTTTG TGAATTTGTT GTTACTGTTT TTCTGTGAAG CACATACATG   1550
TATGTGGGAG GTAAAGGGGC ATTCCAGTTG CTCCAGTCAC TCCCTCTATA   1600
GCCATACTGT CTTGTTTTCT GTAACTCAGG TTAGGTTTTG GTCTCTATTC   1650
TCTGCTGCAG AAAAGGAAAG AAGGAGTGGG GGAAATGGAG CCTGAAGAGT   1700
TGGGGCAGAT AGACCTCAGC CAAACTGGCT GGGTTTTGAG GAGTCATGTT   1750
CTTTCTTCCC TTGAAGGGGA AAGAGTTTTT TCCACTGGTC ACTTTAAAGT   1800
TTCCCAGCTA TGGGGTGGTA CCAGTTCTGG ACAAGTGCCA CTGCATCATA   1850
GTATGCTCGG AGAATCTGAA CCTTACTCTG AAGATGAAAT TTACTGTTGC   1900
CACTGCCAGG TCACACTGGT GTTTTAAGGA ATACTGGGTG CTTCATATAG   1950
GAACTGAAGG GGTAAACTTA CTAAACCATT CAACCTGTGA TTGGTGATGT   2000
TTTCCTGTCA TTTTAAGAGT CGACACATGG GTGGGGGGGC AGATGTAAAA   2050
AAACTTGTAC AATTTTAAAA TATCACAATT AAACGTGAGC TGGTTTCCCA   2100
AAAAAAAAAA AAAAAAAA            [SEQ ID NO:7]
```

```
                 10          20          30          40          50          60
E124    MVWGHFPLAVFDSLGSGEMADSVKTFLQDLGRGIKDSIWGICTISKL_DARIQQKREEEQR
celf37                    MVKFQIIARDFYHGFIDSFKGITFVRRIREEAKEVKVEPP 70          80          90         100         110         120
E124    RRRASSLLAQRRPQSVERKQESEPRIVSRIFQCCAWNGGVFWFSLLLFYRVFIPVLQSVT
celf37  KPVERTVLMRREKQGIFKRPPEPPKKKDSFLKKKLWQIYAMNIGFLVLWQVCIILGLF 130         140         150         160         170         180
E124    ARIIGDPSLHGDVWSWLEFFLTSIFSALWVLPLFVLSKVVNAIWFQDIADLAFEVSGRKP
celf37  FSFFDRTDLGHNI---GYIL---IIPIFFASRIIQALWFSDISGACMRALKLPP 190         200         210         220         230         240
E124    HPFPSVSKIIADMLFNLLLQALFLIQGMFVSLFPIHLVGOLVSLLHMSLLYSLLYCFEYRW
celf37  PPVVPFSSMLAGTLIISALHQIFFLLIQGMLSQYLPIPLIITPVIVYLHMALLNSMYCFDYFF 250         260         270         280         290         300
E124    FNKGIEMHQRLSNIERNWPYFGFGLPWLSSQQCNPPTLSVAASFLSCFLYSSAPMKQR
celf37  DGYNLSFLRRKDIFESHWPYFLGFGTPL--ALACSISSNMFVNSVIFALLFPFFIITSYP 310
E124    LLEKHIFSSCAYSPWWSF
celf37  ANWNRKYEEEJPKIAFCRISYMFTELVGKFVKSITPTNNPTAARNNAQN
```

R17440

```
  1 gaatggtgga gtgttctggt tcagtctcct cttgttttat cgagtatttta ttcctgtgct
 61 tcagtcgta acagcccgaa ttatcggtga cccatcacta catggagatg tttggtcgtg
121 gctggaattc ttcctcacgt caattttcag tgctctttgg gtgctcccct tgtttgtgct
181 tagcaaagtg gtgaatgcca tttggtttca ggatatagct gacctggcat ttgaggtatc
241 agggaggaag cctcacccat tcctagtgt cagcaaaata attgctgaca tgctctttcaa
301 cctttttgctg caggctcttt tcctcattca gggaatgttt gtgagtctct ttccatcca
361 tctgtcggt cagctggtta gtctcctgca tatgtccctn cttctaactt cactgtaact
421 gctttngaat antcgttggg ttcaataaga aatggcacca gcgggttgtt ctaacatagg
481 aaagggaatt gggcctnact acttt    [SEQ ID NO:11]
```

T31497

```
  1 cttcctcacg tcaattttca gtgctctttn ggtgctcccc ttntttgtgc ttagcaaagt
 61 ggtgaatgcc attnggtttc aggatatagc tgacctggca tttgaggtat cagggaggaa
121 gcctcaccca ttcctagtg tcagcaaaat aattgctgac atgctcttca accttttgct
181 gcaggctctt ttcctcattc agggaatgtt tgtnagtctc tttcccatcc atcttgtngg
241 tcagctggtt agtctcctgc atatgtccct tcnctactca atgtactgct ttgaatatcg
301 ttggttttcaa taaaggaat tgaaatgcac cagcggttgt ttaacatagg aaaggaattg
361 ggccttacta ctttgggttt ggtttgccct tggcttttct nacagcaatg cagtccctcat
421 atattgatca gtgctgcc    [SEQ ID NO:12]
```

H85229

```
  1 cagggaggaa gcctcaccca ttccctagtg tcagcaaaat aattgctgac atgctcttca
 61 acctttttgct gcaggctctt ttcctcattc agggaatgtt tgtgagtctc tttcccatcc
121 atcttgtcgg tcagctggtt agtctcctgc atatgtccct tctctactca ctgtactgct
181 ttgaatatcg ttgtttcaat aaaggaattg aaatgcacca gcggttgtct aacatagaaa
241 ggaattggcc ttactacttt gggttggtt tgccctttgcc ctatcctctt tccttnttc attatcaggc
301 cctcatatat tatcagtgcc tgccttttct ctatcctctt tccttnttc attatcaggc
361 gccaatggaa ggcaaagacc cnggggcaaa gcatattctc ttccagttgg nggcc [SEQ ID NO:13]
```

```
  1 tccagtgttg tgcttggaat ggtggagtgt tctggttcag tctcctcttg ttttatcgag
 61 tatttattcc tgtgcttcag tcggtaacag cccgaattat cggtgaccca tcactacatg
121 gagatgtttg gtcgtggctg gaattcttcc tcacgtcaat tttcagtgct ctttgggtgc
181 tccccttgtt tgtgcttagc aaagtggtga atgccatttg gtttcaggat atagctgacc
241 tggcatttga ggtatcaggg aggaagcctc acccattccc tagttgtcag caaaataatt
301 gctgacatng ctcttncaac cttttnactt gcaggc [SEQ ID NO:14]
```

Z25927

```
  1 ggcatttgag gtatcaggga ggaagcctca cccattccct agtgtcagca aaataattgc
 61 tgacatgctc ttcaaccttt gctgcaggc tcttttcctc attcagggaa tgtttgtgag
121 tctctttccc atccatcttg tcggtcagct ggttagtctc ctgcatatgt cccttctcta
181 ctcactgtac tgctttgaat atcgttggtt caataaagga attgaaatgc accagcggtt
241 gtctaacata gaaggaatt ggccttacta cttgcttggg tttgccttgg cttttctcac
301 agcaatgcag tctcatatat atcagtggtg ct [SEQ ID NO:15]
```

N36667

```
  1 cagggaggaa gcctcaccca ttccctagtg tcagcaaaat aattgctgac atgctcttca
 61 acctttgct gcaggctctt ttcctcattc agggaatgtt tgtgagtctc tttcccatcc
121 atcttgtcgg tcagctggtt agtctcctgc atatgtccct tctctactca ctgtactgct
181 ttgaatatcg ttggttcaat aaaggaattg aaatgcacca gcggttgtct aacatagaaa
241 ggaattggcc ttactacttt gggtttggtt tgccc [SEQ ID NO:16]
```

N35767

```
  1 gatatagctg acctggcatt tgaggtatca gggaggaagc ctcacccatt ccctagtgtc
 61 agcaaaataa ttgctgacat gctcttcaac cttttgctgc aggctctttt cctcattcag
121 ggaatgtttg tgagtctctt tcccatccat cttgtcggtc agctggttag tctcctgcat
181 atgtcccttc tctactcact gtactgcttt gaatatcgtt ggttcaataa aggaattgaa
241 atgcaccagc ggttgtctaa catagaaa [SEQ ID NO:17]
```

FIG. 7B

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 10 base pairs
        ( B ) TYPE: nucleic acid (C) STRANDEDNESS: single
(D) TOPOLOGY: linear (xi) SEQUENCE DESCRIPTION: SEQ ID NO:1:

TAGCAAGTGC  10

(2) INFORMATION FOR SEQ ID NO:2:

(i) SEQUENCE CHARACTERISTICS:
(A) LENGTH: 10 base pairs
(B) TYPE: nucleic acid
(C) STRANDEDNESS: single
(D) TOPOLOGY: linear (xi) SEQUENCE DESCRIPTION: SEQ ID NO:2:

GGCTAATGCC  10

(2) INFORMATION FOR SEQ ID NO:3:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:3:

GACTCACAAA CATCCCCTGA ATAAGG  26

(2) INFORMATION FOR SEQ ID NO:4:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:4:

CTCCCTGATA CTTCAAATGC CAAGTC  26

(2) INFORMATION FOR SEQ ID NO:5:

(i) SEQUENCE CHARACTERISTICS:
(A) LENGTH: 76 base pairs
(B) TYPE: nucleic acid
(C) STRANDEDNESS: single
(D) TOPOLOGY: linear (xi) SEQUENCE DESCRIPTION: SEQ ID NO:5:

CCCTCCATGA TCAAAGCTTA TGGTTTGGGG GCACTTCCCT CTAGCTGTAT  50

TTGATAGTCT GGGCAGTGGA GAGATG  76

(2) INFORMATION FOR SEQ ID NO:6:

(i) SEQUENCE CHARACTERISTICS:
(A) LENGTH: 49 base pairs
(B) TYPE: nucleic acid
(C) STRANDEDNESS: single
(D) TOPOLOGY: linear (xi) SEQUENCE DESCRIPTION: SEQ ID NO:6:

TCTGTAAGCT TTGCTTTGCT TTAAAAAGAC CACCAAGGAG AAGAGGCGC  49

(2) INFORMATION FOR SEQ ID NO:7:

(i) SEQUENCE CHARACTERISTICS:
(A) LENGTH: 2118 base pairs
(B) TYPE: nucleic acid ( C ) STRANDEDNESS: single
( D ) TOPOLOGY: linear ( x i ) SEQUENCE DESCRIPTION: SEQ ID NO:7:

```
TGAACCCGGG   ACGCGAAAGG   CGGCAGGGGC   AGGCCTGGCG   GCGGCGCGCG        50
GGACTCAGGC   TTTCCCCAGG   CCCTCCATGA   TGAATGGTTT   GGGGGCACTT       100
CCCTCTAGCT   GTATTTGATA   GTCTGGGCAG   TGGAGAGATG   GCTGACAGTG       150
TCAAAACCTT   TCTGCAGGAC   CTTGGCAGGG   GAATCAAAGA   CTCCATCTGG       200
GGCATCTGTA   CCATCTCAAA   GCTAGATGCT   CGGATCCAGC   AGAAGAGAGA       250
GGAACAGCGT   CGAAGAAGGG   CAAGTAGCCT   CTTGGCCCAG   AGGAGACCCC       300
AGAGTGTAGA   GCGGAAGCAA   GAGAGTGAAC   CACGTATTGT   TAGTAGAATT       350
TTCCAGTGTT   GTGCTTGGAA   TGGTGGAGTA   TTCTGGTTCA   GTCTCCTCTT       400
GTTTTATCGA   GTGTTTATTC   CTGTACTTCA   GTCAGTAACA   GCCCGGATTA       450
TTGGAGATCC   ATCACTTCAT   GGAGATGTTT   GGTCATGGCT   GGAATTCTTC       500
CTCACATCAA   TTTTCAGTGC   TCTTTGGGTG   CTCCCCCTGT   TTGTGCTTAG       550
CAAAGTTGTG   AATGCCATTT   GGTTCCAAGA   TATAGCTGAC   TTGGCATTTG       600
AAGTATCAGG   GAGGAAACCT   CATCCATTCC   CCAGTGTCAG   CAAAATAATT       650
GCTGACATGC   TCTTCAACCT   TTTGCTACAG   GCACTTTTCC   TTATTCAGGG       700
GATGTTTGTG   AGTCTCTTCC   CCATCCATCT   TGTGGGTCAG   CTGGTTAGTC       750
TGCTGCATAT   GTCTCTTCTC   TATTCACTGT   ACTGCTTTGA   GTACCGTTGG       800
TTCAACAAAG   GAATTGAAAT   GCACCAGCGA   TTGTCGAACA   TAGAAAGGAA       850
TTGGCCTTAC   TACTTTGGGT   TTGGCTTGCC   TTGGCTTTCC   TCACAGCAAT       900
GCAATCCTCC   TACATTATCA   GTGGCTGCCT   CTTTTCTATC   CTGTTTCCTT       950
TATTCATCAT   CAGCGCCAAT   GAAGCAAAGA   CTCCTGGAAA   AGCATATCTT      1000
TTCCAGTTGC   GCCTATTCTC   CTTGGTGGTC   TTTTTAAGCA   ACAGACTTTT      1050
CCACAAGACC   GTCTACCTGC   AGTCAGCCCT   GAGCAGCTCG   TCCTCTGCAG      1100
AGAAATTCCC   TTCGCCACAT   CCTTCTCCGG   CCAAACTGAA   AGCTGCTGCA      1150
GGCCATTGAG   CCCTGCTGTC   AAAGGGGTGG   GTGGGACTGG   GTGGAGGATG      1200
TGGCAGCTCT   TTTCTCTGTT   TTCCTCCCCC   TGCCGTGGAA   GGCAGAACCC      1250
ACTGCCAAGG   GCCCTCTGCA   TAGTCCCTTG   TCTTTGAATT   GGAATCTTCC      1300
TGACTCCAGT   ATATGGATTT   TTACCACCAC   CCTAGGTCTG   TAAGGACCAG      1350
TTTTCCAGCT   GTTTTTTTAG   CACTTGCCAG   CTCCTGTGCC   TGGACTGATT      1400
GATTTGAGTA   CTTTTTTTCC   CCTTTCCTTG   TGTCATTTAC   CCTCCCACTT      1450
CCTCCTGCCT   TCCAGCACCC   CTGGATGAAT   GGGCTTTGTA   ATTTTAACTG      1500
TTGTATTTTG   TGAATTTGTT   GTTACTGTTT   TTCTGTGAAG   CACATACATG      1550
TATGTGGGAG   GTAAAGGGGC   ATTCCAGTTG   CTCCAGTCAC   TCCCTCTATA      1600
GCCATACTGT   CTTGTTTTCT   GTAACTCAGG   TTAGGTTTTG   GTCTCTATTC      1650
TCTGCTGCAG   AAAAGGAAAG   AAGGAGTGGG   GGAAATGGAG   CCTGAAGAGT      1700
TGGGGCAGAT   AGACCTCAGC   CAAACTGGCT   GGGTTTTGAG   GAGTCATGTT      1750
CTTTCTTCCC   TTGAAGGGGA   AAGAGTTTTT   TCCACTGGTC   CATTTAAAGT      1800
TTCCCAGCTA   TGGGGTGGTA   CCAGTTCTGG   ACAAGTGCCA   CTGCATCATA      1850
GTATGCTCGG   AGAATCTGAA   CCTTACTCTG   AAGATGAAAT   TTACTGTTGC      1900
```

```
CACTGCCAGG TCACACTGGT GTTTTAAGGA ATACTGGGTG CTTCATATAG              1950

GAACTGAAGG GGTAAACTTA CTAAACCATT CAACCTGTGA TTGGTGATGT              2000

TTTCCTGTCA TTTTAAGAGT CGACACATGG GTGGGGGGGC AGATGTAAAA              2050

AAACTTGTAC AATTTTAAAA TATCACAATT AAACGTGAGC TGGTTTCCCA              2100

AAAAAAAAAA AAAAAAA                                                  2118
```

( 2 ) INFORMATION FOR SEQ ID NO:8:

( i ) SEQUENCE CHARACTERISTICS:
        ( A ) LENGTH: 317 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Met  Val  Trp  Gly  His  Phe  Pro  Leu  Ala  Val  Phe  Asp  Ser  Leu  Gly
                    5                   10                          15

Ser  Gly  Glu  Met  Ala  Asp  Ser  Val  Lys  Thr  Phe  Leu  Gln  Asp  Leu
                    20                  25                          30

Gly  Arg  Gly  Ile  Lys  Asp  Ser  Ile  Trp  Gly  Ile  Cys  Thr  Ile  Ser
                    35                  40                          45

Lys  Leu  Asp  Ala  Arg  Ile  Gln  Gln  Lys  Arg  Glu  Glu  Gln  Arg  Arg
                    50                  55                          60

Arg  Arg  Ala  Ser  Ser  Leu  Leu  Ala  Gln  Arg  Arg  Pro  Gln  Ser  Val
                    65                  70                          75

Glu  Arg  Lys  Gln  Glu  Ser  Glu  Pro  Arg  Ile  Val  Ser  Arg  Ile  Phe
                    80                  85                          90

Gln  Cys  Cys  Ala  Trp  Asn  Gly  Gly  Val  Phe  Trp  Phe  Ser  Leu  Leu
                    95                  100                         105

Leu  Phe  Tyr  Arg  Val  Phe  Ile  Pro  Val  Leu  Gln  Ser  Val  Thr  Ala
                    110                 115                         120

Arg  Ile  Ile  Gly  Asp  Pro  Ser  Leu  His  Gly  Asp  Val  Trp  Ser  Trp
                    125                 130                         135

Leu  Glu  Phe  Phe  Leu  Thr  Ser  Ile  Phe  Ser  Ala  Leu  Trp  Val  Leu
                    140                 145                         150

Pro  Leu  Phe  Val  Leu  Ser  Lys  Val  Val  Asn  Ala  Ile  Trp  Phe  Gln
                    155                 160                         165

Asp  Ile  Ala  Asp  Leu  Ala  Phe  Glu  Val  Ser  Gly  Arg  Lys  Pro  His
                    170                 175                         180

Pro  Phe  Pro  Ser  Val  Ser  Lys  Ile  Ile  Ala  Asp  Met  Leu  Phe  Asn
                    185                 190                         195

Leu  Leu  Leu  Gln  Ala  Leu  Phe  Leu  Ile  Gln  Gly  Met  Phe  Val  Ser
                    200                 205                         210

Leu  Phe  Pro  Ile  His  Lys  Val  Gly  Gln  Leu  Val  Ser  Leu  Leu  His
                    215                 220                         225

Met  Ser  Leu  Leu  Tyr  Ser  Leu  Tyr  Cys  Phe  Glu  Tyr  Arg  Trp  Phe
                    230                 235                         240

Asn  Lys  Gly  Ile  Glu  Met  His  Gln  Arg  Leu  Ser  Asn  Ile  Glu  Arg
                    245                 250                         255

Asn  Trp  Pro  Tyr  Tyr  Phe  Gly  Phe  Gly  Leu  Pro  Trp  Leu  Ser  Ser
                    260                 265                         270

Gln  Gln  Cys  Asn  Pro  Pro  Thr  Leu  Ser  Val  Ala  Ala  Ser  Phe  Lys
                    275                 280                         285

Ser  Cys  Phe  Leu  Tyr  Ser  Ser  Ser  Ala  Pro  Met  Lys  Gln  Arg  Leu
```

Leu Glu Lys His Ile Phe Ser Ser Cys Ala Tyr Ser Pro Trp Trp
                    305                     310                     315

Ser Phe (2) INFORMATION FOR SEQ ID NO:9:

(i) SEQUENCE CHARACTERISTICS:
        (A) LENGTH: 318 amino acids
        (B) TYPE: amino acid
        (C) STRANDEDNESS: single
        (D) TOPOLOGY: linear (xi) SEQUENCE DESCRIPTION: SEQ ID NO:9:

Met Val Trp Gly His Phe Pro Leu Ala Val Phe Asn Ser Leu Gly
                     5                      10                       15

Ser Gly Glu Met Ala Asn Ser Val Lys Thr Phe Leu Gln Asn Leu
                    20                      25                       30

Gly Arg Gly Ile Lys Asp Ser Ile Trp Gly Ile Cys Thr Ile Ser
                    35                      40                       45

Lys Leu Arg Asp Ala Arg Ile Gln Gln Lys Arg Glu Glu Gln Arg
                    50                      55                       60

Arg Arg Arg Ala Ser Ser Leu Leu Ala Gln Arg Arg Pro Gln Ser
                    65                      70                       75

Val Glu Arg Lys Gln Glu Ser Glu Pro Arg Ile Val Ser Arg Ile
                    80                      85                       90

Phe Gln Cys Cys Ala Trp Asn Gly Gly Val Phe Trp Phe Ser Leu
                    95                     100                      105

Leu Leu Phe Tyr Arg Val Phe Ile Pro Val Lys Gln Ser Val Thr
                   110                     115                      120

Ala Arg Ile Ile Gly Asp Pro Ser Leu His Gly Asp Val Trp Ser
                   125                     130                      135

Trp Leu Glu Phe Phe Leu Thr Ser Ile Phe Ser Ala Leu Trp Val
                   140                     145                      150

Leu Pro Leu Phe Val Leu Ser Lys Val Val Asn Ala Ile Trp Phe
                   155                     160                      165

Gln Asp Ile Ala Asp Lys Ala Phe Glu Val Ser Gly Arg Lys Pro
                   170                     175                      180

His Pro Phe Pro Ser Val Ser Lys Ile Ile Ala Asp Met Leu Phe
                   185                     190                      195

Asn Leu Leu Leu Gln Ala Leu Phe Leu Ile Gln Gly Met Phe Val
                   200                     205                      210

Ser Leu Phe Pro Ile His Leu Val Gly Gln Leu Val Ser Leu Leu
                   215                     220                      225

His Met Ser Leu Leu Trp Ser Leu Trp Cys Phe Glu Tyr Arg Trp
                   230                     235                      240

Phe Asn Lys Gly Ile Glu Met His Gln Arg Leu Ser Asn Ile Glu
                   245                     250                      255

Arg Asn Trp Pro Tyr Tyr Phe Gly Phe Gly Leu Pro Trp Leu Ser
                   260                     265                      270

Ser Gln Gln Cys Asn Pro Pro Thr Leu Ser Val Ala Ala Ser Phe
                   275                     280                      285

Leu Ser Cys Phe Leu Tyr Ser Ser Ala Pro Met Lys Gln Arg
                   290                     295                      300

Leu Leu Glu Lys His Ile Phe Ser Ser Cys Ala Tyr Ser Pro Trp
                   305                     310                      315

Trp Ser Phe (2) INFORMATION FOR SEQ ID NO:10:

(i) SEQUENCE CHARACTERISTICS:
        (A) LENGTH: 329 amino acids
        (B) TYPE: amino acid
        (C) STRANDEDNESS: single
        (D) TOPOLOGY: linear (xi) SEQUENCE DESCRIPTION: SEQ ID NO:10:

```
Met Val Lys Phe Gln Ile Ile Ala Arg Asp Phe Tyr His Gly Phe
                 5                  10                  15
Ile Asn Ser Phe Lys Gly Ile Thr Phe Val Arg Arg Ile Arg Glu
                20                  25                  30
Glu Glu Ala Lys Glu Val Lys Val Glu Pro Pro Lys Pro Val Glu
                35                  40                  45
Arg Thr Val Leu Met Met Arg Arg Glu Lys Gln Gly Ile Phe Lys
                50                  55                  60
Arg Pro Pro Gly Pro Pro Lys Lys Lys Asp Ser Phe Leu Lys Lys
                65                  70                  75
Leu Tyr Gln Ile Tyr Ala Met Asn Ile Gly Phe Leu Val Leu Trp
                80                  85                  90
Gln Val Cys Ile Leu Gln Gly Leu Phe Phe Ser Phe Phe Asn Arg
                95                 100                 105
Thr Asn Leu Gly His Asn Ile Trp Ser Trp Leu Gly Tyr Ile Leu
               110                 115                 120
Thr Ser Ile Phe Ser Ala Leu Trp Val Leu Ile Ile Pro Ile Phe
               125                 130                 135
Phe Ala Ser Arg Ile Ile Gln Ala Leu Trp Phe Ser Asp Ile Ser
               140                 145                 150
Gly Ala Cys Met Arg Ala Leu Lys Leu Pro Pro Pro Val Val
               155                 160                 165
Pro Ala Ser Ser Met Leu Ala Gly Thr Leu Ile Ser Ala Leu His
               170                 175                 180
Gln Ile Phe Phe Leu Ile Gln Gly Met Leu Ser Gln Tyr Leu Pro
               185                 190                 195
Ile Pro Lys Thr Pro Val Ile Val Tyr Leu His Met Ala Leu Leu
               200                 205                 210
Asn Ser Met Tyr Cys Phe Asp Tyr Phe Phe Asp Gly Tyr Asn Leu
               215                 220                 225
Ser Phe Leu Arg Arg Lys Asp Ile Phe Glu Ser His Trp Pro Tyr
               230                 235                 240
Phe Leu Gly Phe Gly Thr Pro Leu Leu Ser Ala Leu Ala Cys Ser
               245                 250                 255
Ile Ser Ser Asn Met Phe Val Asn Ser Val Ile Phe Ala Leu Leu
               260                 265                 270
Phe Pro Phe Phe Ile Ile Thr Ser Tyr Pro Ala Asn Trp Asn Arg
               275                 280                 285
Lys Tyr Glu Glu Glu Ile Pro Lys Ile Ala Phe Cys Arg Ile Ser
               290                 295                 300
Tyr Met Phe Thr Glu Leu Val Gly Lys Phe Val Lys Ser Ile Thr
               305                 310                 315
Pro Thr Asn Asn Pro Thr Ala Ala Arg Asn Asn Ala Gln Asn
               320                 325
```

( 2 ) INFORMATION FOR SEQ ID NO:11:

( i ) SEQUENCE CHARACTERISTICS:
        ( A ) LENGTH: 505 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

| | | | | | |
|---|---|---|---|---|---|
| GAATGGTGGA | GTGTTCTGGT | TCAGTCTCCT | CTTGTTTTAT | CGAGTATTTA | 50 |
| TTCCTGTGCT | TCAGTCGGTA | ACAGCCCGAA | TTATCGGTGA | CCCATCACTA | 100 |
| CATGGAGATG | TTTGGTCGTG | GCTGGAATTC | TTCCTCACGT | CAATTTTCAG | 150 |
| TGCTCTTTGG | GTGCTCCCCT | TGTTTGTGCT | TAGCAAAGTG | GTGAATGCCA | 200 |
| TTTGGTTTCA | GGATATAGCT | GACCTGGCAT | TGAGGTATC | AGGGAGGAAG | 250 |
| CCTCACCCAT | TCCCTAGTGT | CAGCAAAATA | ATTGCTGACA | TGCTCTTCAA | 300 |
| CCTTTTGCTG | CAGGCTCTTT | TCCTCATTCA | GGGAATGTTT | GTGAGTCTCT | 350 |
| TTCCCATCCA | TCTTGTCGGT | CAGCTGGTTA | GTCTCCTGCA | TATGTCCCTN | 400 |
| CTTCTAACTT | CACTGTAACT | GCTTTNGAAT | ANTCGTTGGG | TTCAATAGGA | 450 |
| AATGGCACCA | GCGGGTTGTT | CTAACATAGG | AAAGGGAATT | GGGCCTNACT | 500 |
| ACTTT | | | | | 505 |

( 2 ) INFORMATION FOR SEQ ID NO:12:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

| | | | | | |
|---|---|---|---|---|---|
| CTTCCTCACG | TCAATTTTCA | GTGCTCTTTN | GGTGCTCCCC | TTNTTTGTGC | 50 |
| TTAGCAAAGT | GGTGAATGCC | ATTNGGTTTC | AGGATATAGC | TGACCTGGCA | 100 |
| TTTGAGGTAT | CAGGGAGGAA | GCCTCACCCA | TTCCCTAGTG | TCAGCAAAAT | 150 |
| AATTGCTGAC | ATGCTCTTCA | ACCTTTTGCT | GCAGGCTCTT | TTCCTCATTC | 200 |
| AGGGAATGTT | TGTNAGTCTC | TTTCCCATCC | ATCTTGTNGG | TCAGCTGGTT | 250 |
| AGTCTCCTGC | ATATGTCCCT | TCNCTACTCA | CTGTACTGCT | TTGAATATCG | 300 |
| TTGGTTTCAA | TAAAAGGAAT | TGAAATGCAC | CAGCGGTTGT | TTAACATAGG | 350 |
| AAAGGAATTG | GGCCTTACTA | CTTTGGGTTT | GGTTTGCCCT | TGGCTTTTCT | 400 |
| NACAGCAATG | CAGTCCTCAT | ATATTGATCA | GTGGCTGCC | | 439 |

( 2 ) INFORMATION FOR SEQ ID NO:13:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

| | | | | | |
|---|---|---|---|---|---|
| CAGGGAGGAA | GCCTCACCCA | TTCCCTAGTG | TCAGCAAAAT | AATTGCTGAC | 50 |
| ATGCTCTTCA | ACCTTTTGCT | GCAGGCTCTT | TTCCTCATTC | AGGGAATGTT | 100 |
| TGTGAGTCTC | TTTCCCATCC | ATCTTGTCGG | TCAGCTGGTT | AGTCTCCTGC | 150 |
| ATATGTCCCT | TCTCTACTCA | CTGTACTGCT | TTGAATATCG | TTGGTTCAAT | 200 |

| | | | | | |
|---|---|---|---|---|---|
| AAAGGAATTG | AAATGCACCA | GCGGTTGTCT | AACATAGAAA | GGAATTGGCC | 250 |
| TTACTACTTT | GGGTTTGGTT | TGCCCTTGGC | TTTTCTCACA | GCAATGCAGT | 300 |
| CCTCATATAT | TATCAGTGGC | TGCCTTTTCT | CTATCCTCTT | TCCTTTNTTC | 350 |
| ATTATCAGGC | GCCAATGGAA | GGCAAAGACC | CNGGGGCAAA | GCATATTCTC | 400 |
| TTCCAGTTGG | NGGCC | | | | 415 |

( 2 ) INFORMATION FOR SEQ ID NO:14:

( i ) SEQUENCE CHARACTERISTICS:
        ( A ) LENGTH: 336 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

| | | | | | |
|---|---|---|---|---|---|
| TCCAGTGTTG | TGCTTGGAAT | GGTGGAGTGT | TCTGGTTCAG | TCTCCTCTTG | 50 |
| TTTTATCGAG | TATTTATTCC | TGTGCTTCAG | TCGGTAACAG | CCCGAATTAT | 100 |
| CGGTGACCCA | TCACTACATG | GAGATGTTTG | GTCGTGGCTG | GAATTCTTCC | 150 |
| TCACGTCAAT | TTTCAGTGCT | CTTTGGGTGC | TCCCCTTGTT | TGTGCTTAGC | 200 |
| AAAGTGGTGA | ATGCCATTTG | GTTTCAGGAT | ATAGCTGACC | TGGCATTTGA | 250 |
| GGTATCAGGG | AGGAAGCCTC | ACCCATTCCC | TAGTTGTCAG | CAAAATAATT | 300 |
| GCTGACATNG | CTCTTNCAAC | CTTTTNACTT | GCAGGC | | 336 |

( 2 ) INFORMATION FOR SEQ ID NO:15:

( i ) SEQUENCE CHARACTERISTICS:
        ( A ) LENGTH: 332 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

| | | | | | |
|---|---|---|---|---|---|
| GGCATTTGAG | GTATCAGGGA | GGAAGCCTCA | CCCATTCCCT | AGTGTCAGCA | 50 |
| AAATAATTGC | TGACATGCTC | TTCAACCTTT | TGCTGCAGGC | TCTTTTCCTC | 100 |
| ATTCAGGGAA | TGTTTGTGAG | TCTCTTTCCC | ATCCATCTTG | TCGGTCAGCT | 150 |
| GGTTAGTCTC | CTGCATATGT | CCCTTCTCTA | CTCACTGTAC | TGCTTTGAAT | 200 |
| ATCGTTGGTT | CAATAAGGA | ATTGAAATGC | ACCAGCGGTT | GTCTAACATA | 250 |
| GAAAGGAATT | GGCCTTACTA | CTTGCTTGGG | TTTGCCTTGG | CTTTTCTCAC | 300 |
| AGCAATGCAG | TCTCATATAT | ATCAGTGGTG | CT | | 332 |

( 2 ) INFORMATION FOR SEQ ID NO:16:

( i ) SEQUENCE CHARACTERISTICS:
        ( A ) LENGTH: 275 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

| | | | | | |
|---|---|---|---|---|---|
| CAGGGAGGAA | GCCTCACCCA | TTCCCTAGTG | TCAGCAAAAT | AATTGCTGAC | 50 |
| ATGCTCTTCA | ACCTTTTGCT | GCAGGCTCTT | TTCCTCATTC | AGGGAATGTT | 100 |
| TGTGAGTCTC | TTTCCCATCC | ATCTTGTCGG | TCAGCTGGTT | AGTCTCCTGC | 150 |
| ATATGTCCCT | TCTCTACTCA | CTGTACTGCT | TTGAATATCG | TTGGTTCAAT | 200 |

-continued

| AAAGGAATTG | AAATGCACCA | GCGGTTGTCT | AACATAGAAA | GGAATTGGCC | 250 |
| TTACTACTTT | GGGTTTGGTT | TGCCC | | | 275 |

( 2 ) INFORMATION FOR SEQ ID NO:17:

( i ) SEQUENCE CHARACTERISTICS:
        ( A ) LENGTH: 268 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

| GATATAGCTG | ACCTGGCATT | TGAGGTATCA | GGGAGGAAGC | CTCACCCATT | 50 |
| CCCTAGTGTC | AGCAAAATAA | TTGCTGACAT | GCTCTTCAAC | CTTTTGCTGC | 100 |
| AGGCTCTTTT | CCTCATTCAG | GGAATGTTTG | TGAGTCTCTT | TCCCATCCAT | 150 |
| CTTGTCGGTC | AGCTGGTTAG | TCTCCTGCAT | ATGTCCCTTC | TCTACTCACT | 200 |
| GTACTGCTTT | GAATATCGTT | GGTTCAATAA | AGGAATTGAA | ATGCACCAGC | 250 |
| GGTTGTCTAA | CATAGAAA | | | | 268 |

APOPTOSIS GENE EI24, COMPOSITIONS, AND METHODS OF USE

FIELD OF THE INVENTION

The present invention relates generally to the field of cell physiology, and more particularly, to apoptosis. Even more particularly, the present invention is related to a novel apoptosis associated protein EI24 and its corresponding gene EI24; to nucleotide sequences encoding EI24; to products and processes involved in the cloning, preparation and expression of genes and nucleotide sequences encoding EI24; to antibodies with specificity to EI24; and to diagnostic and therapeutic uses of the above.

BACKGROUND OF THE INVENTION

"Apoptosis" refers to cell suicide that proceeds by an active, physiological process (Kerr, J. F., et al., Br. J. Cancer 26:239–257 (1972); Wyllie, A. H., Nature 284:555–556 (1980)). Apoptosis plays an important role in developmental processes, including morphogenesis, maturation of the immune system, and tissue homeostasis whereby cell numbers are limited in tissues that are continually renewed by cell division (Ellis, R. E., et al., Annu. Rev. Cell. Biol. 7:663–698 (1991); Oppenheim, R. W., et al., Neurosci. 14:453–501 (1991); Cohen, J. J., et al., Annu. Rev. Immunol. 10:267–293 (1992); Raff, M. C., Nature 356:397–400 (1992)).

In addition to its role in developmental processes, apoptosis is an important cellular safeguard against tumorigenesis (Williams, G. T., Cell 65:1097–1098 (1991); Lane, D. P. Nature 362:786–787 (1993)). Defects in the apoptotic pathway may contribute to the onset or progression of malignancies. Suppression of the apoptotic pathway(s), by a variety of genetic lesions, occurs frequently in a broad range of human tumors. In particular, loss of the p53 tumor suppressor gene function, either through deletion or mutation, occurs in more than 50% of human cancers. p53 gene function is also indicated in normal cell cycle events. Reviews of p53 function include Levine, A. J., et al., Nature 351:453–456 (1991); Hollstein M., et al., Science 253:49–53 (1991); Donehower, et al., Biochem. BioPhys. Acta 1155:181–205 (1993); Lane, D. P. Nature 362:786–787 (1993); Zambetti, et al., FASEB J. 7:855–865 (1993); and Greenblatt M. S., et al., Cancer Res., 54: 4855–4878 (1994).

p53 may exert its tumor suppressor function, at least in part, by directing cells that have sustained genomic damage to undergo apoptosis (Lowe S. W., Jacks T., Housman D. E. and Ruley H. E. (1994) Proc. Natl. Acad. Sci. USA, 91, 2026–2030). p53 is a sequence-specific DNA binding protein that functions both as a transcriptional activator and repressor (Donehower L. A. and Bradley A. (1993) Biochim. Biophys. Acta., 1155, 181–205; Prives C. and Manfredi J. (1993) Genes Dev., 7, 529–534; Fields S. and Jang S. K. (1990) Science, 249, 1046–1048; Raycroft L., Wu H. and Lozano G. (1990) Science, 249, 1049–1051). Although there is some evidence that transcription may not be required in p53-mediated apoptosis (Caelles C., Helmberg A. and Karin M. (1994) Nature, 370, 220–223), several p53-regulated genes have been identified to date (Kastan M. B., Zhan Q., El-Deiry W. S., Carrier F., Jacks T., Walsh W. V., Plunkett B. S., Vogelstein B. and A. J. Fornace Jr. (1992) Cell, 71, 587–597, 1992; El-Deiry W. S., Tokino T., Velculescu V. E., Levy D. B., Parsons R., Trent J. M., Lin D., Mercer W. E., Kinzler K. W. and Vogelstein B. (1993) Cell, 75, 817–825; Barak Y., Juven T., Haffner R. and Oren M. (1993) EMBO J., 12, 461–468; Wu X., Bayle J. H., Olson D. and Levine A. J. (1993) Genes & Dev., 7, 1126–1132; Zambetti G. P., Bargonetti J., Walker K., Prives C. and Levine A. J. (1992) Genes & Dev., 6, 1143–1152; Okamoto K. and Beach D. (1994) EMBO J, 13, 4816–4822; Buckbinder L., Talbott R., Seizinger B. R. and Kley N. (1994) Proc. Natl. Acad. Sci. USA, 91, 10640–10644, and two of these genes, bcl-2 and bax (Miyashita T. and Reed J. (1995) Cell, 80, 293–299; Miyashita T., Krajewski S., Krajewska M., Wang H., Lin H., Hoffman B., Lieberman K. and Reed J. (1994) Oncogene, 9, 1799–1805; Zhan Q., Fan S., Bae I., Guillouf C., Liebermann D. A., O'Connor P. M. and A. J. Fornace Jr. (1994) Oncogene, 9, 3743–3751), have been clearly implicated in apoptosis (Oltvai Z. and Korsmeyer S. (1994) Cell, 79, 189–192).

In addition to cancer, deregulation of apoptosis may contribute to a number of other human diseases. A variety of degenerative disorders may involve aberrant apoptosis, resulting in premature or inappropriate cell death (Barr, P. J., et al., Biotechnology 12:487–493 (1994)) Productive infection by certain viruses may depend on suppression of host cell death by anti-apoptotic viral gene products (Rao, L., et al., Proc. Natl. Acad. Sci. USA 89:7742–7746 (1992); Ray, C. A., et al., Cell 69:597–604 (1992); White, E., et al., Mol. Cell. Biol. 12:2570–2580 (1992); Vaux, D. L., et al., Cell 76:777–779 (1994), and inhibition of apoptosis can alter the course (i.e. lytic vs. latent) of viral infection; Levine, B., et al., Nature 361:739–742 (1993)). Widespread apoptosis of T lymphocytes triggered by HIV infection may, at least in part, be responsible for the immune system failure associated with AIDS (Gougeon M., et al., Science 260:1269–1270 (1993)).

The ability of p53 to suppress tumorigenesis appears linked to its activity as a transcriptional activator, since tumor-derived mutant p53 molecules almost invariably have lost transactivation potential (Kern, S. E., et al., Science 256:827–830 (1992)). Thus, the function of the p53 tumor suppressor appears to depend, at least in part, on the ability to activate the expression of one or more target genes. Genes activated by p53 may in turn mediate one or more aspects of p53's tumor suppressor function, which including cell cycle arrest and apoptosis, depending on the cellular context. Consistent with the notion, certain p53-activated genes identified to date have been implicated in cell cycle control (gadd45, cyclin G, p21/WAF) and at least one p53-activated gene (bax) is linked to the regulation of apoptosis.

Tumor cells frequently have lost wild-type p53 function. Consequently, activation of p53 target genes and associated tumor suppressor functions, such as cell cycle arrest and apoptosis, is defective in cancer cells. Therefore, from the perspective of pharmaceutical development, identification of genes which are regulated (e.g, induced or repressed) by p53 may permit development of agents that activate, restore or suppress p53-dependent tumor suppression functions such as apoptosis or cell cycle regulation, depending on the clinical setting.

SUMMARY OF THE INVENTION

In a broad aspect, the present invention is directed to a gene, termed EI24, whose RNA was induced in NIH3T3 cells following treatment with etoposide. Experiments performed with cells derived from p53-deficient mice demonstrate that induction of the EI24 mRNA is dependent on expression of functional p53 in vertebrate cells including etoposide-treated fibroblasts, and gamma-irradiated thymocytes. Expression of a conditional p53-fusion protein demonstrates that activation of wild-type p53 function in E1A and T24 H-ras-transformed p53-deficient fibroblasts is sufficient for induction of the EI24 mRNA.

The novel EI24 gene and the corresponding EI24 protein of mammals have thus been isolated and characterized, and are described in a number of embodiments herein. The present invention thus relates to an apoptosis associated protein EI24, products and processes involved in the cloning, preparation and expression of genes for EI24; antibodies with specificity to EI24; and nucleotide probes corresponding to the EI24 nucleotide sequence or portions thereof. The EI24 polypeptide is useful for producing antibodies thereto. The antibodies and probes are useful for detecting and isolating EI24 in biological specimens including for example, cells from all human tissues including heart tissue, lung tissue, tumor cells, brain tissue, placenta, liver, skeletal muscle, kidney, and pancreas.

The present invention further relates to species homologs and viral homologs of EI24.

In a particular embodiment, the human EI24 gene has been cloned. The present invention thus relates to the cloning, identification, characterization and sequencing of cDNAs and genomic fragments which encode the EI24 that is present in human cells. The present invention further relates to a method for isolating EI24 partial clones using polymerase chain reaction (PCR) cloning, from diverse human tumor cell lines.

According to the present invention, there are provided genetic sequences encoding EI24. The instant invention also provides for expression vectors containing such genetic sequences, hosts transformed with such expression vectors, and methods for producing the genetically engineered or recombinant EI24.

The present invention also provides antibodies which specifically recognize EI24.

The EI24 cDNA and recombinant protein are useful for making antibodies which specifically recognize EI24. Such antibodies are useful for detecting and isolating EI24 in a biological specimen. The EI24 protein is also useful as a mediator of p53 function, particularly, p53 tumor suppression function, including p53 mediated apoptotic and/or cell cycle control function.

The present invention is further directed to methods for inducing or suppressing p53 mediated functions including apoptosis in individuals suffering from degenerative disorders characterized by inappropriate cell proliferation or inappropriate cell death, respectively. Degenerative disorders characterized by inappropriate cell proliferation include, for example, inflammatory conditions, cancer, including lymphomas, genotypic tumors, etc. Degenerative disorders characterized by inappropriate cell death include, for example, autoimmune diseases, acquired immunodeficiency disease (AIDS), cell death due to radiation therapy or chemotherapy, etc.

The present invention also relates to methods for detecting the presence of EI24 protein, as well as methods directed to the diagnosis of degenerative disorders, which disorders are associated with an increased or decreased level of expression of EI24, as compared to the expected level of EI24 expression in the normal cell population.

The present invention is further directed to methods for monitoring the progress of degenerative disorders associated with increased or decreased levels of expression of EI24, by monitoring EI24 expression.

The present invention also relates to methods for determining whether a disease/degenerative disorder is linked to abnormal EI24 expression, as well as methods for determining the effect of over expression or loss of expression of EI24 in animal models such as transgenic mice and/or homozygous null mice. Methods for determining whether a disease/degenerative disorder is linked to abnormal EI24 expression include analyzing EI24 expression in diseased tissue as compared to normal tissue by for example, Northern and/or Western blots, as well as by other assay methods readily chosen and employed by those of ordinary skill in the art.

The present invention also relates to therapeutic methods and compositions for modulating apoptotic effects by administering EI24 protein, or a mutant or hybrid thereof, or by modulating expression of the EI24 gene, to an individual suffering from a degenerative disorder characterized by inappropriate cell proliferation or inappropriate cell death in order to stabilize inappropriate cell proliferation (i.e., induce apoptosis) or stabilize inappropriate cell death (i.e., suppress apoptosis), respectively, and/or in either case to restore normal cell behavior.

The present invention further relates to functional equivalents including functional fragments of EI24 and/or EI24.

The present invention is also directed to nucleotide probes which can be used to determine the presence of EI24 as well as to identify and isolate homologs including species homologs and viral homologs.

DESCRIPTION OF THE FIGURES

FIG. 2. Complete nucleotide sequence of EI24 cDNA SEQ ID NO:7 and the predicted protein sequence SEQ ID NO:8. The coding region is shown from positions 84 to 1034. The sequence of the 11G10 probe, identified by differential display, is underlined. The accession number for the EI24 sequence submitted to GenBank is U41751.

FIG. 3. Alignment of the EI24 predicted amino acid sequence SEQ ID NO:8 and the CELF37C12.2 sequence from C. elegans SEQ ID NO:10.

FIG. 7. Human Expressed Sequence Tag (EST) DNA sequences having greater than 90% homology with EI24. The descriptions of the EST clones and their GenBank EST database accession numbers are found in Table I SEQ ID NO:11, SEQ ID NO:12, SEQ ID NO:13, SEQ ID NO:14 and SEQ ID NO:15.

DETAILED DESCRIPTION OF THE INVENTION

Figure 1:
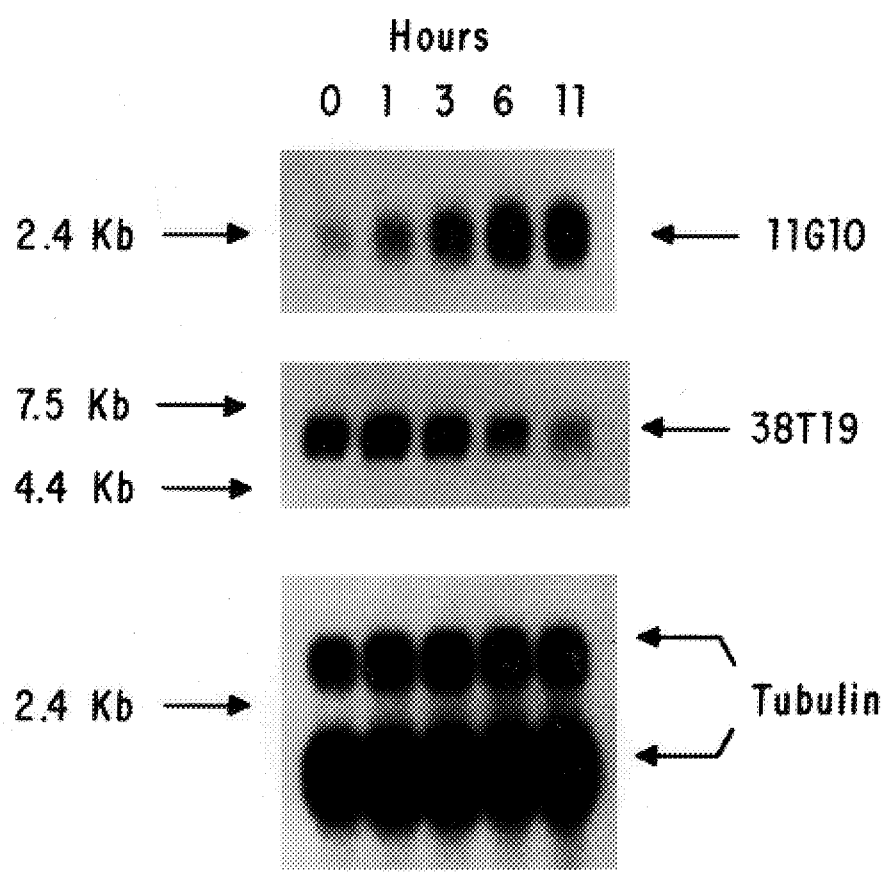
FIG. 1. Northern blot analysis of etoposide-treated murine 3T3 cells using the 11G10 and 38T19 probes. Cells were treated with 50 $\mu$m etoposide and poly-A$^+$ RNA was harvested at the times indicated. Northern blots were probed sequentially with the 11G10 probe, the 38T19 probe and a tubulin probe.

Genetic Engineering of EI24, Functional Equivalents Thereof and Mutants Thereof

This invention comprises amino acid sequences of EI24 or EI24 mutants, genetic sequences coding for such amino acid sequences, expression vehicles containing the genetic sequences, hosts transformed therewith and recombinant EI24 and antisense RNA produced by such transformed host expression. The invention further comprises antibodies directed against EI24 and/or fragments thereof or against EI24 mutants.

The process for genetically engineering such protein sequences, according to the invention, is facilitated through the cloning of genetic sequences which are capable of encoding the peptide and through the expression of such genetic sequences. As used herein, the term "genetic sequences" is intended to refer to a nucleic acid molecule (preferably DNA). Genetic sequences which are capable of encoding the proteins are derived from a variety of sources. These sources include genomic DNA, cDNA, synthetic DNA, and combinations thereof. The preferred source of the genomic DNA or mRNA is human tissue including heart, lung, tumor cells, brain, placenta, liver, skeletal muscle, kidney and pancreas. The mRNA may then be used to obtain cDNA by techniques known to those skilled in the art. Probes may be synthesized based on the nucleotide sequence of EI24 by methods known in the art.

The EI24 protein or fragment genomic DNA of the invention may or may not include naturally occurring introns. Moreover, such genomic DNA may be obtained in association with the 5' promoter region of the EI24 protein gene sequences and/or with the 3' transcriptional termination region. Further, such genomic DNA may be obtained in association with the genetic sequences which encode the 5' non-translated region of the EI24 protein mRNA and/or with the genetic sequences which encode the 3' non-translated region. To the extent that a host cell can recognize the transcriptional and/or translational regulatory signals associated with the expression of the mRNA and protein, the 5' and/or 3' non-transcribed regions of the native gene, and/or the 5' and/or 3' non-translated regions of the mRNA, may be retained and employed for transcriptional and translational regulation. EI24 protein genomic DNA can be extracted and purified from human tissue by means well known in the art (for example, see *Guide to Molecular Cloning Techniques*, S. L. Berger, et al., eds., Academic Press (1987)).

Alternatively, mRNA can be isolated from any cell which produces or expresses the protein, and used to produce cDNA by means well known in the art (for example, see *Guide to Molecular Cloning Techniques*, S. L. Berger, et al., eds., supra. Preferably, the mRNA preparation used will be enriched in mRNA coding for such EI24 protein, either naturally, by isolation from cells which are producing large amounts of the protein, or in vitro, by techniques commonly used to enrich mRNA preparations of specific sequences, including for example sucrose gradient centrifugation, or PCR. cDNA can then be prepared for example, by reverse transcription. The cDNA can then be amplified by PCR using suitable primers.

For cloning into a vector, such suitable DNA preparations (either human genomic DNA or cDNA) are randomly sheared or enzymatically cleaved, respectively, and ligated into appropriate vectors to form a recombinant gene (either genomic or cDNA) library. A DNA sequence encoding the EI24 protein or its functional equivalents may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, for example, by Sambrook J., Fritsch E. F. and Maniatis T. *Molecular Cloning: A Laboratory Manual*; Cold Spring Harbor Laboratory Press: Cold Spring Harbor, N.Y., 1989, (*In: Molecular Cloning, A Laboratory Manual*, Cold Spring Harbor Laboratories, Cold Spring Harbor, N.Y., 2d. ed. (1989)), and are well known in the art.

Libraries containing the EI24 protein clones may be screened and a EI24 clone identified by any means which specifically selects for EI24 protein DNA such as, for example, (a) by hybridization with an appropriate nucleic acid probe(s) containing a sequence specific for the DNA of this protein, or (b) by hybridization-selected translational analysis in which native mRNA which hybridizes to the clone in question is translated in vitro and the translation products are further characterized, or, (c) if the cloned genetic sequences are themselves capable of expressing mRNA, by immunoprecipitation of a translated EI24 or fragment product produced by the host containing the clone.

Oligonucleotide probes specific for the protein which can be used to identify clones to this protein can be designed from knowledge of the amino acid sequence of the EI24 protein. The sequence of amino acid residues in a peptide is designated herein either through the use of their commonly employed three-letter designations or by their single-letter designations. A listing of these three-letter and one-letter designations may be found in textbooks such as *Biochemistry*, 2ed., Lehninger, A., Worth Publishers, New York, N.Y. (1975). When the amino acid sequence is listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence.

Because the genetic code is degenerate, more than one codon may be used to encode a particular amino acid (Watson, J. D., *In: Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., *In: Molecular Biology of the Gene*, 3rd Ed., W. A. Benjamin, Inc., Menlo Park, Calif. (1977)), one or more different oligonucleotides can be identified from the amino acid sequence, each of which would be capable of encoding EI24 or a fragment protein thereof. The probability that a particular oligonucleotide will, in fact, constitute the actual protein coding sequence can be estimated by considering abnormal base pairing relationships and the frequency with which a particular codon is actually used (to encode a particular amino acid) in eukaryotic cells. Such "codon usage rules" are disclosed by Lathe, et al., *J. Molec. Biol.* 183:1–12 (1985). Using the "codon usage rules" of Lathe, a single oligonucleotide sequence, or a set of oligonucleotide sequences, that contains a theoretical "most probable" nucleotide sequence capable of encoding the EI24 protein sequences is identified.

The suitable oligonucleotide, or set of oligonucleotides, which is capable of encoding a fragment of the EI24 protein gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, Calif.) and employed as a probe to identify and isolate the cloned EI24 protein gene by techniques known in the art. Techniques of nucleic acid hybridization and clone identification are disclosed by Maniatis, et al. (*In: Molecular Cloning, A Laboratory Manual*, Cold Spring Harbor Laboratories, Cold Spring Harbor, N.Y. (1982)); Berger, et al., (*In: Guide to Molecular Cloning Techniques*, Academic Press (1988)); Sambrook J., Fritsch E. F. and Maniatis T. *Molecular Cloning: A Laboratory Manual*; Cold Spring Harbor Laboratory Press: Cold Spring Harbor, N.Y., 1989, (*In: Molecular Cloning, A Laboratory Manual*, Cold Spring Harbor Press, Cold Spring Harbor, N.Y., 2d ed. (1989); and by Hames, et al. (*In: Nucleic Acid Hybridization, A Practical Approach*, IRL Press, Washington, D.C. (1985)), which references are herein incorporated by reference. Those members of the above-described gene library which are found to be capable of such hybridization are then analyzed to determine the extent and nature of the EI24 protein encoding sequences which they contain.

To facilitate the detection of the desired EI24 or fragment protein DNA encoding sequence, the above-described DNA probe is labeled with a detectable group or label. Such detectable group or label can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, et al., *J. Mol. Biol.* 113:237 (1977) and by T4 DNA polymerase replacement synthesis as described in, for example, Deen, et al., *Anal. Biochem.* 135:456 (1983).

Alternatively, polynucleotides are also useful as nucleic acid hybridization probes when labeled with a non-radioactive marker such as biotin, an enzyme or a fluorescent or chemiluminescent group. See, for example, Leary, et al., *Proc. Natl. Acad. Sci., USA* 80:4045 (1983); Renz, et al., *Nucl. Acids Res.* 12:3435 (1984); and Renz, M., *EMBO J.* 6:817 (1983).

Thus, the actual identification of the EI24 protein sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the EI24 protein gene.

In an alternative way of cloning the EI24 protein gene, a library is prepared using an expression vector, by cloning DNA or, more preferably, cDNA prepared from a cell capable of expressing the EI24 protein, into an expression vector. The library is then screened for members which express the EI24 protein, for example, by screening the library with antibodies to the EI24 protein.

Preferred EI24 clones according to the invention include the human EI24 cDNA clone designated pKSEI24 1–2 and the composite murine EI24 cDNA clone designated pKSEI24 cl.11. Clones pKSEI24 1–2 and pKSEI24 cl.11 have been deposited under the Budapest Treaty with the American Type Culture Collection (ATCC), 12301 Parklawn Drive, Rockville, Md. 20852, on Mar. 20, 1996, and have been assigned the ATCC Accession Numbers 97487 and 97488, respectively.

The above discussed methods are, therefore, capable of identifying genetic sequences which are capable of encoding EI24 proteins or fragments thereof. In order to further characterize such genetic sequences, and, in order to produce the recombinant protein, it is desirable to express the proteins which these sequences encode Such expression identifies those clones which express proteins possessing characteristics of the EI24 proteins. Such characteristics may include the ability to specifically bind antibody to the EI24 protein and the ability to elicit the production of an antibody or antibodies which are capable of binding to the EI24 protein.

Expression of EI24 protein, Fragments Thereof, Functional Equivalents Thereof, and Mutants Thereof To express the EI24 protein or a functional equivalent, or mutant thereof, transcriptional and translational signals recognizable by an appropriate host are necessary. The cloned EI24 encoding sequences, obtained, for example, through the methods described above, and preferably in a double-stranded form, may be operably linked to sequences controlling transcriptional expression in an expression vector, and introduced into a host cell, either prokaryotic or eukaryotic, to produce recombinant EI24 protein or a functional equivalent thereof. Depending upon which strand of the EI24 encoding sequence is operably linked to the sequences controlling transcriptional expression, it is also possible to express EI24 antisense RNA or a functional equivalent thereof.

Expression of EI24 in different hosts may result in different post-translational modifications which may alter the properties of the EI24. The present invention encompasses the expression of the EI24 protein, or functional equivalent thereof, or EI24 mutant, in prokaryotic or eukaryotic cells, and particularly, eukaryotic expression is preferred.

Preferred prokaryotic hosts include bacteria such as *E. coli*, Bacillus, Streptomyces, Pseudomonas, Salmonella, Serratia, etc. The most preferred prokaryotic host is *E. coli*. Other enterobacteria such as *Salmonella typhimurium* or *Serratia marcescens*, and various *Pseudomonas species* may also be utilized. Under such conditions, the protein may not be glycosylated. The procaryotic host must be compatible with the replicon and control sequences in the expression plasmid.

To express the EI24 protein (or a functional equivalent thereof) or EI24 mutant in a prokaryotic cell (such as, for example, *E. coli, B. subtilis*, Pseudomonas, Streptomyces, etc.), it is necessary to operably link the EI24 encoding sequence to a functional prokaryotic promoter. Such promoters may be either constitutive or, more preferably, regulatable (i.e., inducible or derepressible). Examples of constitutive promoters include the int promoter of bacteriophage lambda, the bla promoter of the Beta-lactamase gene of pBR322, and the CAT promoter of the chloramphenicol acetyl transferase gene of pBR325, etc. Examples of inducible prokaryotic promoters include the major right and left promoters of bacteriophage lambda ($P_L$ and $P_R$), the trp, recA, lacZ, lacI, and gal promoters of *E. coli*, the alpha-amylase (Ulmanen, I., et al., *J. Bacteriol.* 162:176–182 (1985)) and the sigma-28-specific promoters of *B. subtilis* (Gilman, M. Z., et al., *Gene* 32:11–20 (1984)), the promoters of the bacteriophages of Bacillus (Gryczan, T. J., *In: The Molecular Biology of the Bacilli*, Academic Press, Inc., N.Y. (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream of the gene-encoding sequence. Such ribosome binding sites are disclosed, for example, by Gold, L., et al. (*Ann. Rev. Microbiol.* 35:365–404 (1981)).

Especially preferred eukaryotic hosts include vertebrate and particularly mammalian cells either in vivo, in animals or in tissue culture.

Expression of the EI24 in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which infect eukaryotic cells, such as adenovirus, bovine papilloma virus, Simian virus, herpes virus, or the like. Preferably, these regulatory signals are associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA product capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer, et al., *J. Mol. Appl. Gen.* 1:273–288 (1982)); the TK promoter of Herpes virus (McKnight, S., *Cell* 31:355–365 (1982)); the SV40 early promoter (Benoist, et al. *Nature* (*London*) 290:304–310 (1981)); in yeast, the yeast gal4 gene promoter (Johnston, et al. *Proc. Natl. Acad. Sci. USA* 79:6971–6975 (1982); Silver, et al., *Proc. Natl. Acad. Sci. USA* 81:5951–5955 (1984)) or a glycolytic gene promoter may be used.

As is widely known, translation of eukaryotic mRNA is initiated at the codon which encodes the first methionine. For this reason, it is preferable to ensure that the linkage between a eukaryotic promoter and a DNA sequence which encodes the EI24 protein, or a functional equivalent thereof, does not contain any intervening codons which are capable of encoding a methionine. The presence of such codons results either in the formation of a fusion protein (if the AUG codon is in the same reading frame as the EI24 encoding DNA sequence) or a frame-shift mutation (if the AUG codon is not in the same reading frame as the EI24 encoding sequence).

If desired, a fusion product of the EI24 may be constructed. For example, the sequence coding for the EI24 or fragment thereof may be liked to a signal sequence which will allow secretion of the protein from or the compartmentalization of the protein in, a particular host. Such signal sequences may be designed with or without specific protease sites such that the signal peptide sequence is amenable to subsequent removal.

Transcriptional initiation regulatory signals can be selected which allow for repression or activation, so that expression of the operably linked genes can be modulated. Of interest are regulatory signals which are temperature-sensitive, such that by varying the temperature, expression can be repressed or initiated, or which are subject to chemical regulation, e.g., by a metabolite. Also of interest are constructs wherein the EI24 mRNA and antisense RNA are provided in a transcribable form, but with different promoters or other transcriptional regulatory elements such that induction of EI24 mRNA expression is accompanied by repression of antisense RNA expression, and/or repression of EI24 mRNA expression is accompanied by induction of antisense RNA expression.

Translational signals are not necessary when it is desired to express EI24 antisense RNA sequences.

If desired, the non-transcribed and/or non-translated regions 3' to the sequence coding for the EI24 protein can be obtained by the above-described cloning methods. The 3'-non-transcribed region may be retained for its transcriptional termination regulatory sequence elements; the 3'-non-translated region may be retained for its translation termination regulatory sequence elements, or for those elements which direct polyadenylation in eukaryotic cells. Where the native expression control sequence signals do not function satisfactorily in the host cell, then sequences functional in the host cell may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the EI24 DNA construct into the host cell chromosomal DNA, or to allow it to exist in an extrachromosomal form.

If the EI24 DNA encoding sequence and an operably linked promoter are introduced into a recipient eukaryotic cell as a non-replicating DNA (or RNA) molecule, which may either be a linear molecule or a closed covalent circular molecule which is incapable of autonomous replication, then the expression of the EI24 protein may occur through the transient expression of the introduced sequence.

Genetically stable transformants may be constructed with vector systems, or transformation systems, whereby EI24 DNA is integrated into the host chromosome. Such integration may occur de novo within the cell or, in a preferred embodiment, be assisted by transformation with a vector which functionally inserts itself into the host chromosome, for example, with retroviral vectors, transposons or other DNA elements which promote integration of DNA sequences into chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example, the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein, et al., *Miami Wntr. Symp.* 19:265–274 (1982); Broach, J. R., *In: The Molecular Biology of the Yeast Saccharomyces: Life Cycle and Inheritance*, Cold Spring Harbor Laboratory, Cold Spring Harbor, N.Y., pp. 445–470 (1981); Broach, J. R., *Cell* 28:203–204 (1982); Bollon, et al., *J. Clin, Hematol. Oncol.* 10:39–48 (1980); Maniatis, T., *In: Cell Biology: A Comprehensive Treatise*, Vol. 3, "Gene Expression," Academic Pres, N.Y., pp. 563–608 (1980)), and are commercially available. For example, mammalian expression vector systems which utilize the MSV-LTR promoter to drive expression of the cloned gene, and in which it is possible to contransfect with a helper virus to amplify plasmid copy number, and integrate the plasmid into the chromosomes of host cells, have been described (Perkins, et al., *Mol. Cell Biol.* 3:1123 (1983); Clontech, Palo Alto, Calif.).

Once the vector or DNA sequence containing the construct(s) is prepared for expression, the DNA construct (s) is introduced into an appropriate host cell by any of a variety of suitable means, including transfection. After the introduction of the vector, recipient cells are grown in a selective medium, which selects for the growth of vector-containing cells. Expression of the cloned gene sequence(s) results in the production of the EI24 protein, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein is isolated and purified in accordance with conventional conditions, such as extraction, precipitation, chromatography, affinity chromatography, electrophoresis, or the like. Preferred proteins expressed according to the invention are the products of the clone pKSEI24 cl.11 and particularly of the clone pKSEI24 1–2, described herein.

EI24 can be purified by growing the transformed host cells under suitable conditions which are well known in the art, the cells can be harvested and disrupted to extract total cellular protein. The protein can then, for example, be placed on a sizing column such as sepharose or agarose beads, and proteins of the correct molecular weight can be collected. The predicted molecular weight of EI24 is described herein.

Further purification can be effected by use of an anti-EI24 antibody. Such an antibody can be used to immunoprecipitate EI24 proteins from the set of cellular proteins of the correct approximate molecular weight. Such antibodies can, for example, be raised against polypeptides synthesized according to the sequence or subsequences of the sequence shown herein. Alternatively, the antibodies can be raised against fusion proteins, which contain EI24 sequences as well as those of other proteins. After immunoprecipitation, the EI24 proteins can be released from the antibodies to provide a substantially pure preparation of EI24 protein.

The EI24 DNA coding sequences, of the present invention may be used to obtain EI24 antisense RNA genetic sequences, inasmuch as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of a EI24 antisense RNA in the transformed cell. Antisense RNA and its expression may be used to interact with an endogenous EI24 DNA or RNA in a manner which inhibits or represses transcription or translation of the EI24 genes in a highly specific manner. Use of antisense RNA probes to block gene expression is described, for example, in Lichtenstein, C., *Nature* 333:801–802 (1988).

Construction and Identification of Antibodies Raised Against EI24, Functional Equivalents, Fragments, Hybrids, or Mutants Thereof In the following description, reference will be made to various methodologies well-known to those skilled in the art of immunology. Standard reference works setting forth the general principles of immunology include the work of Catty, D., (*Antibodies, A Practical Approach*, Vol. 1, IRL Press, Washington, D.C. (1988)); Klein, J., (*Immunology: The Science of Cell-Noncell Discrimination*, John Wiley & Sons, New York (1982)); Kennett, et al., (*Monoclonal Antibodies, Hybridoma: A New Dimension in Biological Analyses*, Plenum Press, New York (1980)); Campbell, A. ("Monoclonal Antibody Technology," *In: Laboratory Techniques in Biochemistry and Molecular Biology*, Vol. 13 (Burdon, R., et al., eds.), Elsevier, Amsterdam (1984)); and Eisen, H. N. (*In: Microbiology*, 3rd ed. (Davis, B. D., et al., Harper & Row, Philadelphia (1980)).

An antibody is said to be "capable of binding" a molecule if it is capable of specifically reacting with the molecule to thereby bind the molecule to the antibody. The term "epitope" is meant to refer to that portion of a hapten which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab)$_2$ fragments) which are capable of binding an antigen. Fab and F(ab)$_2$ fragments lack the Fc fragment of intact antibody, clear more rapidly from the circulation, and may have less non-specific tissue binding of an intact antibody (Wahl, et al., *J. Nucl. Med.* 24:16–325 (1983)).

The antibodies of the present invention have specificity to one or more epitopes present on the EI24 peptide, or an idiotype thereon. The antibodies of the invention can be polyclonal or monoclonal, provided that they are made with the EI24 polypeptide or fragment thereof as the immunogen. Both of these types of antibodies can be utilized in the applications described herein.

The present antibodies can be used to detect the presence of the EI24 protein in a human tissue sample. The EI24 protein can be detected by contacting the sample with an imaging-effective amount of the detectably labeled appropriate antibody and detecting the label, thereby establishing the presence of the EI24 protein in the sample. Detection can be carried out by imaging in vivo. The EI24 protein can also be detected by known immunoassay techniques, including, for example, RIA, ELISA, etc., using appropriate antibodies according to the invention.

The antibodies of the present invention are prepared by any of a variety of known methods. For example, cells expressing the EI24 protein can be administered to an animal in order to induce the production of serum containing polyclonal antibodies that are capable of binding the EI24 protein. For example, the EI24 protein or fragment thereof is chemically synthesized and purified by HPLC to render it substantially free of contaminants. Such a preparation is then introduced into an animal in order to produce polyclonal antisera of high specific activity.

Polyclonal antibodies can be generated in any suitable animal including, for example, mice, rabbits or goats. The EI24 immunogenic peptide or fragment thereof can be injected by itself or linked to appropriate immunoactivating carriers, such as Keyhole's limpet hemocyanin (KLH). See *Antibodies, A Practical Handbook*, Vols. I and II, D. Catty, ed., IRL Press, Washington, D.C. (1988).

Monoclonal antibodies can be prepared in various ways using techniques well understood by those having ordinary skill in the art. For example, monoclonal antibodies can be prepared using hybridoma technology (Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., *In: Monoclonal Antibodies and T-Cell Hybridomas*, Elsevier, N.Y., pp. 563–681 (1981)); *Monoclonal Antibodies—Hybridomas: A New Dimension in Biological Analysis*, edited by Roger H. Kennett, et al., published by Plenum Press (1980). In general, such procedures involve immunizing an animal with the EI24 protein, or a fragment thereof. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands, et al., *Gastroenterology* 80:225–232 (1981). The hybridoma cells obtained through such a selection are then assayed to identify clones which secrete antibodies capable of binding the EI24 protein.

Through application of the above-described methods, additional cell lines capable of producing antibodies which recognize epitopes of the EI24 protein can be obtained.

For example, additional hybridomas which produce monoclonal antibodies which enable the detection of the EI24 protein can be easily produced and isolated with minimal screening. Hybridomas producing monoclonal antibodies specific for epitopes which are found on the EI24 protein are most effectively produced by first immunizing an animal from which hybridomas can be produced such as, for example, a Balb/c mouse, with initial subcutaneous injections of Freund's adjuvant, followed by booster injections within a few days. The fusion can be carried out using any of the techniques commonly known to those of ordinary skill in the art. The screening of the hybridomas to determine which ones are producing monoclonal antibodies specific for a peptide is straightforward and can be accomplished in a standard ELISA or RIA format. For example, in an RIA screening format the culture supernatant, or ascites fluid from a hybridoma producing monoclonal antibody is reacted with $^{125}$I-peptide. The isolation of other hybridomas secreting mAbs of the same specificity as those described herein can be accomplished by the technique of anti-idiotypic screening. Potocmjak, et al., *Science* 215:1637 (1982). Briefly, an anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb raised against the EI24 protein or fragment thereof to which an anti-Id is being prepared. The immunized animal will recognize and respond to the idiotypic determinants of the immunizing antibody by producing an antibody to these idiotypic determinants (the anti-Id antibody).

By using an anti-Id antibody which is specific for idiotypic determinants on a given mAb, it is then possible to identify other B cell or hybridoma clones sharing that idiotype. Idiotypic identity between the antibody product of two clones makes it highly probable that the antibody products of the two clones recognize the same antigenic epitopes.

The anti-Id antibody may also be used as an "immunogen" to induce an immune response in yet another animal, producing a so-called anti-anti-Id antibody. The anti-anti-Id may be epitopically identical to the original mAb which induced the anti-Id.

Thus, by using antibodies to the idiotypic determinants of a mAb, it is possible to identify other clones expressing antibodies of identical specificity.

Accordingly, mAbs generated against the EI24 protein may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for the antigen epitope. The anti-Id mAbs thus have their own idiotypic epitopes, or "idiotopes" structurally similar to the epitope being evaluated.

For replication, the hybridoma cells of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Of special interest to the present invention are antibodies which are produced in humans, or are "humanized" (i.e., non-immunogenic in a human) by recombinant or other technology such that they will not be antigenic in humans, or will be maintained in the circulating serum of a recipient for a longer period of time.

Humanized antibodies may be produced, for example by replacing an immunogenic portion of an antibody with a corresponding, but non-immunogenic portion (i.e., chimeric antibodies) (Robinson, et al., International Patent Publication PCT/US86/02269; Akira, et al., European Patent Application 184,187; Taniguchi, M., European Patent Application 171,496; Morrison, et al., European Patent Application 173,494; Neuberger, et al., PCT Application WO 86/01533, Cabilly, et al., European Patent Application 125,023; Better, et al., *Science* 240:1041–1043 (1988); Liu, et al., *Proc. Natl. Acad. Sci. USA* 84:3439–3443 (1987); Liu, et al., *J. Immunol.* 139:3521–3526 (1987); Sun, et al., *Proc. Natl. Acad. Sci. USA* 84:214–218 (1987); Nishimura, et al., *Canc. Res.* 47:999–1005 (1987); Wood, et al., *Nature* 314:446–449 (1985)); Shaw, et al., *J. Natl. Cancer Inst.* 80:1553–1559 (1988). General reviews of "humanized" chimeric antibodies are provided by Morrison, S. L. (*Science*, 229:1202–1207 (1985)) and by Oi, et al., *BioTechniques* 4:214 (1986)).

Suitable "humanized" antibodies can be alternatively produced as described by Jones, et al., *Nature* 321:552–525 (1986); Verhoeyan, et al., *Science* 234:1534 (1988), and Beidler, et al., *J. Immunol.* 141:4053–4060 (1988).

The EI24 protein, fragments thereof, hybrids thereof, EI24 mutants, or antibodies thereto can be utilized in immunoassays for the detection of the EI24 protein in a human tissue sample. For example, antibodies against the EI24 protein can be used to detect the EI24 protein in a human tissue sample. The immunoassays can be competitive or sandwich, as is otherwise well known and they all depend on the formation of antibody-antigen immune complex. These assays are well known to those of skill in the art.

For purposes of the assays, the antibody or antigen can be immobilized or labeled. There are many carriers to which the antibody/antigen can be bound for immobilization and which can be used in the present invention. Well-known carriers include but are not limited to glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding the antibody or antigen, or will be able to ascertain such, using routine experimentation.

Depending on the particular embodiment of the invention, one or more of the antibodies or antigen(s) peptide(s) will be coupled with a detectable label such as an enzyme, radioactive isotope, fluorescent compound, chemiluminescent compound, or bioluminescent compound.

Those of ordinary skill in the art will know of other suitable labels for binding to the antibodies or antigen(s) peptide(s) or will be able to ascertain such using routine experimentation. Furthermore, the binding of these labels to the antibodies or antigen(s) can be done using standard techniques commonly known to those of ordinary skill in the art.

The antibodies or antigen peptide(s) can be bound to an enzyme. This enzyme, in turn, when later exposed to its substrate will react with the substrate in such a manner as to produce a chemical moiety which can be detected, as, for example, by spectrophotometric or fluorometric means. Examples of enzymes that can be used to detectably label are amylate dehydrogenase, staphylococcal nuclease, delta-5-steroidisomerase, yeast alcoholdehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholinesterase.

The presence of an antibody or antigen can also be detected by labeling the antibody or antigen with a radioactive isotope. The presence of the radioactive isotope can be determined by such means as the use of a gamma counter or a scintillation counter. Isotopes which are particularly useful are $^3$H, $^{125}$I, $^{32}$P, $^{35}$S, $^{14}$C, $^{51}$Cr, $^{36}$Cl, $^{57}$Co, $^{59}$Fe, $^{75}$Se, and $^{152}$Eu.

It is possible to detect the presence of the antibody or antigen by labeling the antibody or antigen peptide with a fluorescent compound. When the fluorescently labeled antibody or antigen peptide is exposed to light of the proper wavelength, its presence can then be detected due to fluorescence of the dye. Among the most common fluorescent labeling compounds are fluorescein isothiocyanate, rhodamine, phycoerythrin, phycocyanin, allophycocyanin, o-phthaldehyde, and fluorescamine.

Another way in which the antibody or antigen can be detectably labeled is by coupling it to a chemiluminescent compound. The presence of the chemiluminescent-tagged antibody or antigen peptide is then determined by detecting the presence of luminescence that arises during the course of a chemical reaction. Examples of particularly useful chemiluminescent labeling compounds are luminol, isoluminol, aromatic-acridinium ester, imidaxole, acridinium salt, and oxalate ester.

Likewise, a bioluminescent compound may also be used to label the antibody or antigen peptide. Bioluminescence is a special type of chemiluminescence which is found in biological systems and in which a catalytic protein increases the efficiency of the chemiluminescent reaction. The presence of a bioluminescent binding partner would be determined by detecting the presence of luminescence. Important bioluminescent compounds for purposes of labeling are luciferin, luciferase, and aequorin.

The antibodies or antigen peptide(s) for use in the assay of the invention are ideally suited for the preparation of a kit. Such a kit may comprise a carrier means being compartmentalized to receive in close confinement one or more container means such as vials, tubes, and the like, each of said container means comprising one of the separate elements to be used in the method.

For example, one of the container means may comprise a first antibody bound to an insoluble or partly soluble carrier. A second container may comprise soluble, detectably-labeled second antibody, in lyophilized form or in solution. The carrier means may also contain a third container means comprising a detectably labeled third antibody in lyophilized form or in solution. Such a kit can be used for sandwich assays.

In addition, the carrier means may also contain a plurality of containers each of which comprises different, predetermined amounts of the EI24 peptide. These latter containers can then be used to prepare a standard curve into which can be used to interpolate the results obtained from the sample containing the unknown amount of the EI24 protein.

Imaging can be carried out in vitro or in vivo. In vitro imaging can be done with the labels mentioned previously.

In vivo imaging is done with diagnostically effective labeled antibodies. The term "diagnostically effective" means that the amount of detectably labeled antibody administered is sufficient to enable detection of the site of EI24 protein presence when compared to a background signal.

Generally, the dosage of detectably-labeled antibody or antigen(s) for diagnosis will vary depending on considerations such as age, condition, sex, and extent of disease in the patient, counterindications, if any, and other variables, to be adjusted by the individual physician. Dosage can very from 0.01 mg/kg to 2,000 mg/kg, preferably 0.1 mg/kg to 1,000 mg/kg.

The term "diagnostically labeled" means that the antibody has attached to it a diagnostically detectable label.

There are many different imaging labels and methods of labeling known to those of ordinary skill in the art. Examples of the types of labels which can be used in the present invention include radioactive isotopes and paramagnetic isotopes.

For diagnostic in vivo imaging, the type of detection instrument available is a major factor in selecting a given radionuclide. The radionucleotide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionucleotide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140–200 ke V range, which may be readily detected by conventional gamma cameras.

For in vivo diagnosis, radionucleotides may be bound to antibody or antigen either directly or indirectly by using an intermediary functional group. Intermediary functional groups which are often used to bind radioisotopes which exist as metallic ions to antibody or antigen are diethylentriaminepentaacetic acid (DTPA) and ethlenediaminetetracetic acid (EDTA). Typical examples of metallic ions which can be bound to immunoglobulins are $^{99m}$Tc, $^{123}$I, $^{111}$In, $^{131}$I, $^{97}$Ru, $^{67}$Cu, $^{67}$Ga, $^{72}$As, $^{89}$Zr, and $^{201}$Tl.

The antibodies used in the method of the invention can also be labeled with paramagnetic isotopes for purposes of in vivo diagnosis. Elements which are particularly useful (as in magnetic resonance imaging (MRI) techniques) in this manner include $^{157}$Gd, $^{55}$Mn, $^{162}$Dy, $^{52}$Cr, and $^{56}$Fe.

Preparations of the imaging antibodies for administration include sterile aqueous or non-aqueous solutions, suspensions, and emulsions. Examples of non-aqueous solvents are propyleneglycol, polyethyleneglycol, vegetable oil such as olive oil and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, and inert gases and the like. See, generally, *Remington's Pharmaceutical Science*, 16th ed. Mac Eds. 1980.

Of course, the expressed EI24 protein is an intracellular protein. Accordingly, those of skill will recognize that in vivo diagnostic and therapeutic methods employing the antibodies of the invention may require some mechanism by which such antibodies can detect EI24 in the cell. One such method is to introduce the antibodies or fragments thereof into the cell itself across the cell membrane. This may be accomplished, for example, by attaching the antibody to a ligand for which the target cell contains receptor sites. The antibody can thus be transported into the cell membrane or across the cell membrane along with the ligand. Suitable ligands include growth factors and cytokines that are internalized upon receptor binding. Suitable growth factors include epidermal growth factor (EGF), tumor growth factor alpha (TGF-α), fibroblast growth factor (FGF), insulin, and insulin-like growth factors 1 and 2 (TGF-1 and -2). Suitable cytokines include G-CSF, GM-CSF, erythropoietin, IL-1 and IL-2. It is noted that there are also receptors that carry nutrients and vitamins into cells. These nutrients are suitable for use as ligands in the present invention and include foliate, dihdrofoliate, tetrahydrofoliate and vitamin B12.

The choice of a carrier ligand will depend on several factors, as those of skill will appreciate. These include, for example, the kinetics of the ligand and its receptor, and of overall transport, which may include passive or active, with actively transported ligands preferred. The means of attaching the antibody to the ligand also will vary within limits, and may be, for example, covalent or ionic, bearing in mind that such attachment should not unacceptably alter ligand-receptor affinity.

Examples of receptors suitable for such applications include the receptor for low density lipoprotein (LDL), which has been shown to contain all the information necessary for receptor endocytosis, Davis et al., *J. Cell Biol.* 107(6/3): Abstr. No. 3112 (1988), as well as known brain-specific receptors such as those for dopamine. In this regard, it will be appreciated that the ligand may itself be an antibody or fragment specific for the receptor, to which may be conjugated the antibody of the invention.

Moreover, those of skill may find it particularly desirable to employ antibody fragments of the invention (such as, for example, Fab or F(ab')$_2$ fragments), which are less likely to interfere with the ligand-receptor interaction, and may be more easily transported across the cell membrane. Single-chain antibodies may prove preferable for these and other reasons, as will be appreciated by those of skill.

When an antibody is to be transported into the cell's membrane or into the cell as described above, it will be preferred to diagnostically or therapeutically label the antibody in such a way that the label will be relatively more effective when the antibody is bound to its antigenic site on the EI24 protein. This may accomplished, for example, by employing a label which becomes active or detectable as a result of formation of the antigen-antibody complex. Alternatively, the antibody itself may be labeled in such a way that antigen-antibody complex formation induces a conformational change in the antibody to expose or more fully expose the previously unexposed or less fully exposed label. All of the above criteria, and others, will be apparent to those of skill in carrying out these aspects of the invention.

It is also possible to utilize liposomes having the antibodies of the present invention in their membranes to specifically deliver the antibodies to the target area. These liposomes can be produced so that they contain, in addition to the antibody, such therapeutic agents as drugs, radioisotopes, lectins and toxins, which would act at the target site.

Pharmaceutical Compositions

Pharmaceutical compositions containing a therapeutically effective amount of the EI24 protein, functional equivalents, fragments and/or hybrids and/or mutants thereof, as well as vectors containing cDNA encoding one or more of the foregoing, are useful for treating patients suffering from disorders in which p53 mediated functions such as tumor suppression and cell cycle arrest are indicated, including but not limited to degenerative disorders characterized by inappropriate cell death or inappropriate cell proliferation.

Hybrids of EI24 with one or more other proteins exhibit enhanced, decreased or intermediate effects on p53 mediated functions such as apoptosis induction or suppression activity as compared to the activity of EI24 alone. These hybrids can be readily selected, produced and employed by one or ordinary skill in the art. Pharmaceutical compositions according to the invention thus will contain a therapeutically effective amount of the EI24 protein, functional equivalents, fragments and/or hybrids and/or mutants thereof, and may optionally contain one or more pharmaceutically acceptable carriers and/or excipients, known to those of ordinary skill in the art. Administration, dosage and frequency, and length of the course of treatment can be readily optimized for a particular patient by one of ordinary skill in the art. For example, the present pharmaceutical composition can be formulated as sterile aqueous or non-aqueous suspensions or emulsions, as described above in Section IV, for example for solutions for intravenous administration.

Therapeutic Applications

The EI24 protein, functional equivalents, fragments and/or hybrids and/or mutants thereof as well as vectors containing cDNA encoding the foregoing are useful for treating cells, tissues or organs in which p53 mediated function is relevant to cell, tissue or organ state, including but not limited to states characterized by inappropriate cell death, inappropriate cell proliferation or inappropriate cell persistence. Particular disorders may involve different cell types whereby it may be desirable to induce apoptosis in one cell type while suppressing apoptosis in the other. In addition, agents which modulate EI24 gene expression can be used therapeutically according to the present invention.

The therapeutic agents of the present invention can be administered as discussed above with the requirement that the agent must cross the cell membrane. The therapeutic agent can be administered alone, in combination with or during the course of treatment with other acceptable therapies known in the art for treating a particular disorder. For example, the present therapeutic agents can be administered to induce apoptosis in a cancer patient who is also undergoing classic cancer therapy including, for example, radiation therapy, chemotherapy, and treatment with anti-cancer drugs including, for example, topoisomerase inhibitors, alkylating agents, antimetabolites, and hormone antagonists. Further, the present therapeutic agents can also be administered concurrently with gene therapy. For example, the present therapeutic agents can be administered to a patient suffering from a degenerative disorder of the central nervous system while the patient is concurrently undergoing gene therapy to replenish neutrophic hormones.

Premature widespread apoptosis (inappropriate cell death) causes much of the damage associated with degenerative disorders including, for example, AIDs, chemotherapy and radiation, and tissue atrophy. In AIDs patients, lymphocytes are activated even in the asymptomatic phase of the HIV infection, and those cells die prematurely by apoptosis.

Those of skill will appreciate that administration of the various proteins of the invention to particular target cells or tissues, as described herein, is intended to comprehend the administration of the proteins themselves as well as the expression by the target cells or tissues of the nucleotide sequences encoding those proteins by various known means and in accordance with the teachings of the present specification. Methods for the in vivo treatment of vertebrates including humans at the gene level are known in the art and described, for example, in A. M. L. Lever and P. Goodfellow, Eds., "Gene Therapy," British Medical Bulletin 51(1): 1–242, Churchill Livingstone, Pub., Edinburgh (1995).

Degenerative disorders characterized in inappropriate cell proliferation include cancer, autoimmune disorders, tissue hypertrophy, and inflammatory disorders including inflammation arising from acute tissue injury including, for example, acute lung injury. Cancers arise when changes in DNA cause the anomalous accumulation of cells. The comparative rates of cell division and cell deaths determine how fast a cancer grows. Some cancer cells divide more slowly than normal cells, but the cancer may still expand because of prolonged cell life span. Apoptosis is an efficient method for preventing malignant transformation because it removes cells with genetic lesions. Defective apoptosis can promote cancer development, both by allowing accumulation of dividing cells and by obstructing removal of genetic variants with enhanced malignant potential. The present therapeutic agents, as well as vectors containing cDNA encoding the one or more of the foregoing, can be administered to cancer patients to induce apoptosis.

Many types of cancer can be treated by the administration of the present therapeutic agents, including for example, carcinomas, sarcomas, and leukemia/lymphomas, including for example, carcinomas such as adenocarcinomas, squamous carcinomas, carcinoma of the organs including breast, colon, head, neck, etc.; sarcomas including chondrosarcoma, melanosarcoma, etc.; and leukemia and lymphomas including acute lymphomatic leukemia, acute myelogenous leukemia, non-Hodgkin's lymphoma, Burkitt's lymphoma, B-cell lymphomas, T-cell lymphomas, etc. Other conditions amenable to treatment using the present therapeutic agent include fungal infections. Preferred according to the invention are cancers in which p53 function is altered.

The present therapeutic agents can be used to treat autoimmune diseases. Random gene recombination and somatic hypermutation can potentially generate autoreactive T and B lymphocytes throughout life. Under normal conditions immature lymphocytes that bind autoantigens die by apoptosis. However, a defect in the deletion of these lymphocytes predisposes one to autoimmunity.

The present therapeutic agents can be administered to patients suffering from autoimmune disorders to induce apoptosis in autoreactive T lymphocytes, for example, in patients suffering systemic lupus erythematosus. Other autoimmune diseases amenable to treatment by suppressing or inducing apoptosis through the administration of the present therapeutic agents include, for example, rheumatoid arthritis, myasthenia gravis, Grave's disease, Hashimoto's thyroiditis, insulin-resistent diabetes, allergic rhinitis, asthma, functional autonomic abnormalities, juvenile insulin-dependent diabetes, Addison's disease, idiopathic hypoparathyroidism, spontaneous infertility, premature ovarian failure, pemphigus, Bullous pemphigoid, primary biliary cirrhosis, autoimmune hemolytic anemia, idiopathic thrombocytopenic purpura, idiopathic neutropenia, Goodpasture's syndrome, rheumatoid arthritis and Sjogren's syndrome.

The present therapeutic agents can be used to treat inflammation resulting from acute lung injury, by inducing apoptosis. The disease process begins with an explosive inflammatory response in the alveolar wall. In the aftermath of the resulting tissue destruction, extensive fibroproliferation of the alveolar air space ensues, consisting of fibroblasts, capillaries and their connective tissue products. Fukuda, Y., et al., *Am. J. Pathol.* 126:171–182 (1987). The present therapeutic agents can also be used to treat degenerative disorders due to premature or excessive cell loss during aging which can lead to organ disfunction and disease. Such degenerative disorders include degenerative diseases of the central nervous system due to aging or other factors which result in the death of neurons. The present therapeutic agents containing EI24 mutant protein or hybrids thereof can be administered to a patient suffering from such a degenerative disorder to suppress apoptosis. Further, the present therapeutic agents can be administered concurrently with gene therapy to provide genes encoding neutrophic hormones including, for example, nerve growth factor. Other conditions amenable to treatment utilizing the present therapeutic agents include, for example, Alzheimer's disease.

The present therapeutic agents can be administered to the desired target cell as discussed below, for example, by choosing a receptor on the target cell surface which is specific for that cell type. The present therapeutic agents can be administered alone or in combination with other acceptable drug therapies. Further, the present therapeutic agents can be administered concurrently with other acceptable therapies specific for the particular degenerative disorder being treated. For example, the present therapeutic agents can be administered concurrently with chemotherapeutic agents, gene therapy, or the like. Therapeutic agents according to the invention must cross the cell membrane.

One method for introducing the therapeutic agents of the invention into the cell's membrane or into the cell itself is by attaching the agent to a ligand for which the target cell contains receptor sites. The agent can thus be transported into the cell membrane or across the cell membrane along with the ligand.

The choice of a carrier ligand will depend on several factors, as discussed herein and known to those of skill. Suitable tissue-specific receptors include: Brain: nerve growth factor receptor (NGF-R); breast: prolactin receptor; stomach: gastrin receptor; skin: melanocyte stimulating hormone receptor (MSH-R), liver: asialoglycoprotein receptor; thyroid: thyroid stimulating hormone receptor (TSH-R); ovaries: luteinizing hormone receptor (LH-R), testis: human chorionic gonadotrophin receptor (hCG-R), T-cells: T-cell receptors; B cells: CD19; lung hyaluronate receptor CD44 isoform 4V (J. Cell. Biol. 124, 7182, 1994). In this regard, it will be appreciated that the ligand may be an antibody or fragment specific for the receptor, to which may be conjugated the EI24 protein of the invention.

It may be desirable to employ active EI24 fragments according to the invention which are less likely to interfere with the ligand-receptor interaction, and which may be more easily transported across the cell membrane.

When a protein is to be transported across the cell's membrane or into the cell as described above and the ligand is an antibody, it will be preferred to diagnostically or therapeutically label the protein in such a way that the label will be relatively more effective when the protein is bound, such as, for example, by means analogous to those described herein in the context of antibody transport.

It is also possible to utilize liposomes having the proteins of the present invention in their membrane to specifically deliver the EI24 proteins to the target area. These liposomes can be produced so that they contain, in addition to the EI24 protein, such other therapeutic agents including drugs, radioisotopes, lectins and toxins, which would be released at the target site.

A preferred manner for administering the EI24 encoding nucleotide sequences (and their functional equivalents and/or hybrids and/or mutants) for diagnostic or therapeutic purposes is by the use of viral vectors. Suitable viral vectors for gene transfer include retroviruses (reviewed in Miller, et al., Methods Enzymol. vol. 217, p.581–599 (1993)) including human immunodeficiency virus (HIV), adenovirus derivatives (for examples see Erzurum, et al. Nucleic Acids Res. Vol. 21, p.1607–12 (1993); Zabner, et al., Nat. Genet. Vol. 6, p.75–83 (1994); Davidson, et al., Nat. Genet. vol. 3, p.219–223 (1993)) adeno-associated virus (AAV), (i.e. see Flotte, et al., Proc. Natl. Acad. Sci. vol. 90, p.10613–7 (1993)) and Herpes virus vectors (i.e. see Anderson, et al., Cell Mol. Neurobiol. vol. 13, p.503–15 (1993)). Other suitable viruses can be readily selected and employed by those of ordinary skill in the art. Other methods for DNA delivery include liposome mediated gene transfer (Alton, et al., Nat. Genet. vol. 5, p. 135–42 (1993); Nabel, et al., Proc. Natl. Acad. Sci USA vol. 90, p. 11307–11 (1993)).

The use of viral vectors for introduction of genes into mammalian cells is also reviewed, for example, in Varmus, *Science* 240(4858):1427 (1988); Eglitis et al., *BioTechniques* 6,7:608 (1988); Jaenisch, *Science* 240(4858):1468 (1988); and Bernstein et al., *Genet. Eng.* (N.Y.) 7:235 (1985).

For the purposes of the present invention, it may be preferred to employ an attenuated viral or retroviral strain. Thus, for example, it is possible to use as vectors for the DNA sequences of the invention retroviruses having attenuated cytopathicity, such as HIV-$2_{ST}$ (Kong et al., *Science* 240(4858):1525 (1988)) or HIV-$2_{UC1}$ (Evans et al., *Science* 240(4858):1523 (1988)), which enter neural cells by a CD4-dependent mechanism (Funke et al., *J. Exp. Med.* 165:1230 (1987)). The neurobiology of HIV infections is described, for example, in Johnson et al., *FASEB J.* 2(14):2970 (1988). Those of skill will be able to target different cell populations having known susceptibilities to viruses by the exercise of routine skill. For example, CD4 is known to have a variant transcript in the human brain, with its highest content in forebrain (Maddon et al., *Cell* 47:333 (1986). Possible methods to target retroviral gene expression to specific cell types are reviewed by Boris-Lawrie and H. Temin Curr. Opin. Genet. Dev. vol. 3, p.102–9 (1993).

Ideally, then, the choice of a gene delivery system will be made by those of skill, keeping in mind the objectives of efficient and stable gene transfer, with an appropriate level of gene expression, in a tissue-appropriate manner, and without any adverse effects. See, for example, Wolff et al., *Rheum. Dis. Clin. North Am.* 14(2):459 (1988). With respect to delivery to a central nervous system target, many viral vectors, including HIV, offer the advantage of being able to cross the blood-brain barrier (Johnson et al., *FASEB J.* 2(14):2970 (1988)).

Diagnostic Applications

Antibodies raised against the EI24 protein, fragments, functional equivalents, or hybrids or mutants thereof can be used to detect the EI24 protein in a human tissue sample, as well as to diagnose degenerative disorders associated with the expression of the EI24 protein. Further, such antibodies can also be used to monitor the progress of degenerative disorders associated with the expression of the EI24 protein.

Any source of human cells is suitable for use in the diagnostic testing in the present invention. The cells can be isolated from any human tissue including for example, heart, lung, tumor cells, brain, placenta, liver, skeletal muscle, kidney and pancreas. Extraction of proteins from the cell sample may be performed by any of the many means known in the art. For example, cells may be lysed by a detergent by mechanical means. If desired, nucleic acids can be removed from the cell preparation by enzymatic digestion or by precipitation with agents such as streptomycin. Such means are well known in the art.

Antibodies can be generated which are immunoreactive with the EI24 proteins by the methods set forth herein. Appropriate antibodies can then be screened using the natural gene products of EI24.

The extracted proteins from the cell sample may be contacted with the antibody under suitable conditions for antibody-antigen complex formation. Generally, such conditions are physiological conditions. The protein extract may be bound to a solid support such a nitrocellular filter or a microtiter plate.

The antibody will generally bear a label which is a radio label, a florescent label, or an enzyme conjugate which under appropriate conditions produces, for example, a colored reaction product. Antibodies and antibody labeling are described herein and known to those of skill. Alternatively, if the antibody is not labeled, it can be detected by means of a second antibody from another species which is reacted with the first antibody. Suitable assay techniques, labels and means of detection are discussed herein.

A parallel sample to the test sample is employed to provide the control. The control sample consists of an equivalent amount of proteins extracted from cells, preferably in the same manner as those of the test sample. The amount of protein can readily be determined by employing techniques well known in the art, including, for example, the Lowry or Bradford techniques. The cells used for preparing the control sample may be selected from cells of the same cell type as the test cells, isolated from a normal human not suffering from the degenerative disorder from which the human from which the test sample was taken suffers, cells of the same cell type as the test sample isolated from an established normal cell line, and cells from the human who is being tested, which cell type is different from the cell type of the test cells.

Test samples can also be screened for elevated levels of mRNA transcribed from the EI24 gene, according to methods well known in the art. For example, RNA extracted from B-cells may be used, or alternatively mRNA may be isolated from total cellular RNA. The mRNA may be purified, for example, by affinity chromatography on oligo (dT cellulose) which binds to the poly (A) tract at the 3' end of most mRNA. As is well known to those skilled in the art, it is essential that ribonuclease activity be minimized during preparation and assaying.

A DNA probe may be selected from any of the protein coding sequences of the EI24 gene. Preferably, the probe will be selected from sequences of the 5' or 1st exon of the gene, so that all three species of RNA can be detected. Preferably, the probe contains at least 15 nucleotides of the EI24 sequence. In order to perform the hybridization, it is desirable that the probe be single stranded. Thus, if the probe is double stranded, it should be denatured to a single stranded form. Means for denaturing are well known in the art, including alkali or heat treatment. The probe can then be contacted with the RNA derived from the cell sample under conditions where homologous RNA-DNA hybrids form and are stable. Such conditions are well known in the art. Means for detecting hybrids are many and well known, but often involve the use of radiolabeled probes and nucleases which degrade single stranded DNA. Other methods known in the art may be used.

Control samples can be derived from any of these cell sources described above for use in the antibody diagnostic tests. Samples and controls should preferably be prepared in parallel under similar conditions.

The diagnostic methods and compositions of the present invention are useful for determining whether a disease/degenerative disorder is linked to abnormal EI24 expression, as well as for determining the effect of over expression or loss of expression of EI24 in animal models such as transgenic mice and/or homozygous null mice. Methods for determining whether a disease/degenerative disorder is linked to abnormal EI24 expression include analyzing EI24 expression in diseased tissue as compared to normal tissue by for example, Northern and/or Western blots, as well as by other assay methods readily chosen and employed by those of ordinary skill in the art. Once it has been determined that a disease/degenerative disorder is linked to abnormal EI24 expression, the disease/disorder can be diagnosed in an individual.

As used herein, the term "host" is meant to include not only prokaryotes, but also eukaryotes such as yeast and filamentous fungi, as well as plant and animal cells. The term includes an organism or cell that is the recipient of a replicable expression vehicle.

The term "substantially homologous" as used herein refers to the ability of a first DNA sequence encoding EI24 to hybridize to a second DNA sequence encoding the foregoing, under stringent conditions, for example, at about 0.1× sodium citrate sodium chloride buffer (SSC) at a temperature of about 65° C.

The term "substantially pure" means that the protein or molecule of interest is essentially free from any other detectable biological constituents.

As used herein, a "functional equivalent" of the EI24 protein is a protein which possesses a biological activity or immunological characteristic substantially similar to a biological activity or immunological characteristic of non-recombinant EI24. The term "functional equivalent" is intended to include the "fragments," "variants," "analogues," "homologues," or "chemical derivatives" of a molecule which possess the biological activity of the EI24 protein of the invention.

A "fragment" of a molecule such as EI24 is meant to refer to any variant of the molecule which possess the biological activity of the EI24 protein. A "variant" of a molecule is meant to refer to a molecule substantially similar in structure and biological activity or immunological characteristics to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical. An "analog" of a molecule is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are described, for example, in Remington's Pharmaceutical Sciences (1980). Procedures for coupling such moieties to a molecule are well known in the art.

By the term "anti-antibody" is intended an antibody directed against antigenic determinants on another antibody. By the term "anti-idiotypic antibody" is intended an antibody directed against an idiotypic determinant of another antibody. By the term "idiotope" is intended an idiotypic determinant, i.e., an antigenic determinant on a variable domain of an immunoglobulin molecule. By the term "idiotype" is intended a set of one or more idiotopes that distinguish a clone of immunoglobulin producing cells from other clones. Idiotypes occur in the variable domains of immunoglobulin molecules and may be within, near to, or outside of the antigen binding site; antibodies to idiotypes located within or near the antigen biding site will prevent the immunoglobulin from combining with the antigen. By the term "idiotype-anti-idiotype network" is intended a B-cell regulatory mechanism. Activation of a B cell results in a clone of plasma cells producing immunoglobulin of a single idiotype, which, because it was previously present in very small quantities, can be recognized as "nonself" and results in the production of anti-idiotypic antibodies directed against its idiotypic determinants. There can also be anti-anti-idiotypic antibodies directed against the second antibodies, antibodies directed against them, and so forth. These antibodies react with antigen receptors on B cells and T helper and suppressor cells, as well as with circulating antibodies, to enhance or suppress production of the initial antibody by various mechanisms.

By the term "administration" is intended any mode of administration which results in the delivery of the therapeutic agent across the cell membrane and into the desired cell. The site of administration and cells will be selected by one of ordinary skill in the art based upon an understanding of the particular degenerative disorder being treated. In addition, the dosage, dosage frequency, and length of course of treatment, can be determined and optimized by one of ordinary skill in the art depending upon the particular degenerative disorder being treated. The particular mode of administration can also be readily selected by one of ordinary skill in the art and can include, for example, oral, intravenous, subcutaneous, intramuscular, etc., with the requirement that the therapeutic agent cross the cell membrane. The therapeutic agent of the present invention can be the EI24 protein and/or functional equivalents thereof and/or EI24 hybrids or EI24 mutants and/or a vector containing cDNA encoding the foregoing.

By the term "therapeutic agent" is intended the EI24 protein, fragments, functional equivalents and/or hybrids or mutants thereof as well as vectors containing cDNA encoding any of the foregoing. The present therapeutic agent can be administered alone or in combination with and/or concurrently with other suitable drugs and/or courses of therapy.

By the term "degenerative disorder" is intended for purposes of this invention, any disorder characterized by inappropriate cell proliferation, inappropriate cell death, inappropriate cell persistence, or in some cases, a combinationof one or more of these. Preferred according to the invention are degenerative disorders in which p53 function is altered. By the term "inappropriate cell proliferation" is intended a statistically significant increase in cell number as compared to the proliferation of that particular cell type in the normal population. Also included are disorders whereby a cell is present and/or persists in an inappropriate location, e.g., the presence of fibroblasts in lung tissue after acute lung injury. For example, such cells include cancer cells which exhibit the properties of invasion and metastasis and are highly anaplastic. Such cells include but are not limited to, cancer cells including, for example, tumor cells.

By the term "inappropriate cell death" is intended a statistically significant decrease in cell number as compared to the presence of that particular cell type in the normal population. Such under representation may be due to a particular degenerative disorder, including, for example, AIDS (HIV), which results in the inappropriate death of T-cells, autoimmune diseases which are characterized by inappropriate cell death. By the term "inappropriate cell persistence" is intended a statistically significant persistence in cell number as compared to the presence of that particular cell type in the normal population. Such persistence may be due to p53 mediated alterations in cell cycle arrest as compared to normal cells. By the term "autoimmune disease" is intended a disorder caused by an immune response directed against self antigens. Such diseases are characterized by the presence of circulating autoantibodies or cell-mediated immunity against autoantigens in conjunctions with inflammatory lesions caused by immunologically competent cells or immune complexes in tissues containing the autoantigens. Such diseases include systemic lupus, erythematosus (SLE), rheumatoid arthritis.

By the term "suppression" is intended for the purposes of this invention the result achieved by administering an amount of a therapeutic agent containing EI24 hybrids or EI24 mutants thereof effective to suppress apoptosis in an individual suffering from a degenerative disorder characterized by inappropriate cell death. Suppression of apoptosis is achieved when the numbers of the particular affected cell type remain stable or increase in number to a level within the range observed in the normal cell population. By the term "stable" is intended the state achieved when a statistically significant decrease in cell number is no longer observed in the individual being treated, as compared to the cell number observed at the onset of the course of treatment.

By the term "induction" is intended for the purposes of this invention the result achieved by the administration of an amount of a therapeutic agent containing the EI24 of the invention effective to induce apoptosis in cells of an individual suffering from a degenerative disorder characterized by inappropriate cell proliferation. The induction of apoptosis is achieved when cell numbers remain stable or decrease to a level within the range observed in the normal cell population. By the term "stable" is intended the state achieved during the course of treatment when a statistically significant increase in cell proliferation is no longer observed as compared to the cell number observed at the onset of the course of treatment. One of ordinary skill in the art can readily determine whether the induction of apoptosis has been achieved.

Particularly preferred uses of the compositions and methods of the present invention are those which involve p53 mediated function. Examples of such p53 mediated functions include but are not limited to tumor suppression and cell cycle arrest, and are described, for example in Levine, A. J., et al., *Nature* 351:453–456 (1991); Hollstein M., et al., *Science* 253:49–53 (1991); Donehower, et al., *Biochem. BioPhys. Acta* 1155:181–205 (1993); Lane, D. P. *Nature* 362:786–787 (1993); Zambetti, et al., *FASEB J.* 7:855–865 (1993); and Greenblatt M. S., et al., *Cancer Res.*, 54: 4855–4878 (1994). EI24 expression appears to be affected by p53, and accordingly, preferred embodiments of the invention include those in which this relationship is of diagnostic or therapeutic import. Particularly preferred according to the invention is the use of the compositions of the invention in screening assays, as described herein, allowing the identification of agents which themselves are capable of mediating p53 or EI24 function in cells which may be vertebrate cells, preferably mammalian cells, and more preferably, human cells.

By the term "normal cell behavior" is intended for the purposes of this invention, cells in which apoptosis proceeds normally. Normal cell behavior is observed in an organism which is able to remove senescent, damaged, or abnormal cells that could interfere with organ function or develop into tumors. Apoptosis which proceeds normally represents a coordinated cellular response to noxious stimuli that are not immediately lethal.

By the term "patient" or "individual" is intended for the purposes of the present invention, animals, including humans and mammals, who suffer from a degenerative disorder.

By the term "EI24 protein" is intended for the purposes of the present invention both the isolated naturally occurring and isolated recombinantly produced protein (i.e., synthetic EI24) which exhibits, inter alia, p53 induced expression in human tissue including, for example, tumor cells and established human cell lines, and from tissues of other invertebrate and vertebrate animals including mammals. This term includes any analog, homolog, mutant or derivative of isolated naturally occurring EI24 including fragments having less than the naturally occurring number of amino acids, such as partial fragments of natural or synthetic EI24 which retain the biological or immunological characteristics of the polypeptide disclosed in this application. This term also includes any peptide which contains the sequence of an isolated naturally occurring EI24 protein, or analog or homolog thereof, together with one or more flanking amino acids, which retains the biological or immunological characteristics of the EI24 protein of the invention.

The present invention pertains to both the expression of full-length EI24 and of functional derivatives of this protein, including allelic variants of EI24 and species or viral homologs of EI24. Species homologs can be identified, isolated and recombinantly produced using the present nucleotide probes and procedures as described herein, being methods well known in the art. Further, one of ordinary skill in the art can readily determine whether a particular peptide is a functional equivalent of EI24 using methods well known in the art.

More specifically, this term includes proteins encoded by the nucleotide sequence as shown in FIG. 2, and proteins having the amino acid sequence as shown in FIG. 2, allelic variants, species homologs and viral homologs thereof, as well as functional derivatives thereof including fragments which retain the biological characteristics of EI24, and proteins that are substantially homologous thereto, which retain the biological or immunological characteristics of the EI24 protein of the invention.

The following Examples are offered by way of illustration, not by way of limitation.

EXAMPLES

Materials and Methods

Cell Culture. Murine NIH3T3 cells were cultured in DMEM supplemented with 10% iron-fortified bovine calf serum, penicillin (5 U/ml), streptomycin (50 $\mu$g/ml) and L-glutamine (4 mM). Etoposide (Sigma Chemical Co., St. Louis, Mo.) was prepared as a 100 mM solution in DMSO, and used at a final concentration of 50 $\mu$M.

Differential display. Sub-confluent 3T3 cells were treated with etoposide (50 $\mu$M). Total cellular RNA was isolated by lysing cells with guanidinium thiocyanate, as described previously (Sambrook J., Fritsch E. F. and Maniatis T. *Molecular Cloning: A Laboratory Manual*; Cold Spring Harbor Laboratory Press: Cold Spring Harbor, N.Y., 1989).

Total RNA samples were treated with DNase I using the MessageClean kit (GenHunter, Brookline, Mass.) according to the manufacturer's instructions. Reverse transcription and PCR were performed as described previously (Liang P. and Pardee A. B. (1992) *Science*, 257, 967–971), using the RNAmap kit (GenHunter). Four different 3'-primers ($T_{12}$NG, $T_{12}$NA, $T_{12}$NT, $T_{12}$NC) were used in combination with 20 different 10 bp 5'-primers (AP1 to AP20) for PCR amplification, to generate a unique set of PCR products for each RNA population. PCR products were resolved on denaturing polyacrylamide gels, and those that appeared to be differentially expressed were isolated from the gels, re-amplified, and labeled with $^{32}$P-dCTP for northern blot analysis. PCR products which hybridized to differentially expressed RNA's, probe 11G10 (3'-primer $T_{12}$NG and 5'-primer AP10 or 5'-TAGCAAGTGC) [SEQ ID NO:1] and probe 38T19 (3'-primer $T_{12}$NT and 5'-primer AP19 or 5'-GGCTAATGCC) [SEQ ID NO:2], were cloned into pCR II, using the TA Cloning system (Invitrogen, San Diego, Calif.).

Northern blot analysis. Unless indicated otherwise, poly-$A^+$ RNA was extracted from cells using the Fast Track mRNA Isolation system (Invitrogen) according to the supplier's protocol. Northern blot analysis was performed following standard methods (Sambrook J., Fritsch E. F. and Maniatis T. *Molecular Cloning: A Laboratory Manual*; Cold Spring Harbor Laboratory Press: Cold Spring Harbor, N.Y., 1989) using 1.0 $\mu$g of poly-$A^+$ RNA per lane. The northern blot containing poly-$A^+$ RNA (2.0 $\mu$g) from normal human tissues was purchased from Clontech (Palo Alto, Calif.). Northern blots were probed with $^{32}$P-labeled probes and exposed to X-ray film. Autoradiographs were scanned using an LKB 2202 laser densitometer to obtain relative intensities of hybridization signal. The fold-increase or decrease in signal was normalized to the values obtained by hybridization to a control probe.

Isolation of a full length EI24 cDNA. A cDNA library was generated in l-ZAP (Stratagene, La Jolla, Calif.) using poly-$A^+$ RNA prepared from etoposide-treated 3T3 cells. Screening of this library with the probe generated by differential display, yielded one 850 bp clone, representing the 3'-end of the EI24 cDNA. The remaining 5' portion of the cDNA was isolated by screening a lgtll 3T3 library purchased from Clontech.

The extreme 5' end of the EI24 cDNA was cloned using the PCR-based technique 5'-RACE, using the 5'-AMPLIFINDER RACE kit (Clontech), according to the supplier's protocol. Poly-$A^+$ RNA was purified from etoposide-treated 3T3 cells. Two nested primers were designed; 11R8 (5'-GACTCACAAACATCCCCTGAATAAGG) [SEQ ID NO:4] was used for cDNA synthesis, and 11R9 (5'-CTCCCTGATACTTCAAATGCCAAGTC) [SEQ ID NO:4] was used with the Anchor primer for PCR amplification. PCR amplification was carried out for 35 cycles. The resulting PCR products were purified, and cloned into pCR II (above) for DNA sequence analysis. One 500 bp clone obtained extended the largest lgt11 clone by only 19 bp. The composite full length cDNA was assembled from the three separate clones into pBluescript KS II$^+$ (Stratagene) and sequenced. The extreme 5'-end was provided by a 271 bp EcoRI-BamHI fragment isolated from the 5'-RACE clone. This was joined to a 1177 bp BamHI-ScaI fragment obtained from the largest lgt11 clone. Finally, the remaining 3'-untranslated region was cloned as a 709 bp ScaI-XhoI fragment from the single l-ZAP clone. The composite murine EI24 cDNA clone, designated pKSEI24 cl.11, has been deposited with ATCC as accession number 97488.

Isolation of a human EI24 cDNA. A cDNA encoding the human EI24 homolog was cloned by PCR, relying on the high degree of homology to murine EI24. Two oligonucleotide primers, 5'EI24M and 3'EI24, were synthesized with the following DNA sequence:

5'EI24M:

5'-CCCTCCATGATCAAAGCTTATGGTTTGGGGGCACTTCGTGTATTTGATAGTCTGGGCAGTGGAGAGATG-3'[SEQ ID NO:5]

3'EI24:

5'-TCTGTAAGCTTTGCTTTGCTTTAAAAAGACCACCAAGGAG[SEQ ID NO:6]

5'EI24M corresponds to the first 19 amino acids encoded by the murine Ei24 cDNA, which was determined to be sufficiently homologous to the human cDNA to permit PCR amplification. 3'EI24 corresponds to the 3' end of the human EI24 open reading frame, based on partial EI24 sequences deposited in the GenBank EST database.

A human EI24 cDNA clone was obtained by PCR amplification of cDNA prepared from Jurkat cells with the above primers. The PCR product was cloned into the HindIII site of pBluescript KS. This human EI24 clone, designated pKSEI24 1–2, has been deposited with ATCC as accession number 97487.

Isolation of p53$^{+/+}$ and p53$^{-/-}$ thymocytes and Northern blot analysis. Thymocytes were isolated from 4-week old wild-type and p53-null mice (C57BL/6×129/sv genetic background) (Jacks T., Remington L., Williams B. O., Schmitt E. M., Halachmi S., Bronson R. T. and Weinberg R. A. (1994) *Current Biology*, 4, 1–7) and placed in DME supplemented with 10% fetal bovine serum and 25 mM HEPES pH 7.2. The cells were incubated at 37° C. following either no treatment or exposure to 600 cGy ionizing radiation. At the indicated times post treatment, total RNA was extracted from homogenized thymus tissue using the RNA-ZOL B method according to manufacture's instructions (Biotecx Laboratories, Inc., Houston, Tex.). Approximately 10 mg of each RNA was electrophoretically separated on a 1% agarose/1× MOPS/8.3% formaldehyde gel. The RNAs were then transferred to nylon membranes in 20XSSC and UV cross linked to the membrane before prehybridizing, hybridizing and washing as described previously (Shakleford G. and Varmus H. (1987) *Cell*, 50, 89–95). After hybridizing to a probe containing the entire coding region of the EI24 cDNA, the blot was stripped and rehybridized to a probe complementary to the glyceraldehyde phosphate dehydrogenase (GAPDH) mRNA, as a loading standard for each lane.

E1A and ras transformed mouse embryo fibroblasts and expression of the p53-ER™ fusion protein. Stable cell lines of p53$^{+/+}$ and p53$^{-/-}$ MEFs expressing the oncogenes E1A and T24 H-ras were generated as described previously (Lowe S. W., Jacks T., Housman D. E. and Ruley H. E. (1994) *Proc. Natl. Acad. Sci. USA*, 91, 2026–2030). The plasmid for expression of the p53ER™ fusion protein, pBabe Puro p53ER™ G525R, using the retroviral vector pBabe Puro (Morgenstern J. P. and Land H. (1990) *Nucl. Acids Res.*, 18, 3587–3596), was received as a generous gift from Trevor Littlewood (Imperial Cancer Research Fund, London). In brief, this plasmid contains the ~1.3 kb BamHI fragment of human p53 from pSV53her (Roemer K. and Friedmann T. (1993) *Proc. Natl. Acad. Sci. USA*, 90, 9252–9256) fused to the ligand-binding domain of the murine estrogen receptor carrying a point mutation at amino acid 525 that renders the receptor unable to bind estradiol but able to bind tamoxifen or 4-hydroxy tamoxifen (Danielian P., White R., Hoare S., Fawell S. and Parker M. (1993) *Mol Endocrinol*, 7, 232–240; Littlewood T. D., Hancock D. C., Danielian P. S., Parker M. G. and Evan G. I. (1995) *NAR*, 23, 1686–1690). For induction of wild-type p53 activity, p53ER™ transfected p53$^{-/-}$ cells were treated with 3.3 mM tamoxifen (Sigma).

Results

Identification of mRNAs for etoposide-responsive genes.

Murine NIH3T3 fibroblasts were exposed to etoposide at a concentration (50 μM) which was able to kill the majority of asynchronously growing cells within 24 hours. Under these conditions, cells showed no obvious signs of apoptosis (by microscopic observation) for at least 6 hours, following exposure to etoposide. RNA was isolated from 3T3 cells that had been treated with etoposide for 6 hours, and from non-treated cells. The two populations were compared by the differential display technique (Liang P. and Pardee A. B. (1992) *Science*, 257, 967–971), as described in the Materials and Methods. A total of 25 PCR products, which appeared to be differentially expressed in two independent experiments, were initially identified, and used as probes in northern blots of mRNA from normal and etoposide-treated (6 hours) 3T3 cells. By this analysis, only two of these probes proved to be truly differentially expressed in the drug-treated versus untreated cell populations (not shown). The PCR-derived probe designated 38T19 identified a 5 kb mRNA whose expression was diminished in etoposide-treated cells; and probe 11G10 hybridized to a 2.4 kb mRNA that increased in the etoposide-treated cells.

The differential expression of the mRNA species detected by these two probes was examined more closely by northern blot analysis of 3T3 cells exposed to etoposide for varying lengths of time (FIG. 1). The 2.4 kb mRNA recognized by 11G10 was present at low levels in untreated cells and was rapidly induced upon etoposide treatment, showing a 4-fold increase by 3 hours post treatment. Induction of the 2.4 kb mRNA appeared to be maximal by 6 hours after etoposide exposure, representing a 7-fold increase. The same northern blot was stripped and re-hybridized with the 38T19 probe, which detected a 5 kb mRNA. The levels of this mRNA were highest in untreated cells, and decreased at 6 to 11 hours after etoposide treatment, corresponding to a 4-fold reduction.

The DNA sequence of probe 38T19, which detects the 5 kb mRNA, did not significantly match any sequence in the nucleotide sequence database (not shown). Efforts to clone and characterize a full-length cDNA detected by 38T19 are currently ongoing. We report here the cloning and characterization of the cDNA corresponding to the 2.4 kb mRNA recognized by the 11G10 probe, named EI24, for Etoposide-Induced 2.4 kb MRNA.

Isolation of a full-length EI24 CDNA, and analysis of its sequence.

The 11G10 probe was used initially to isolate a partial (850 bp) EI24 cDNA clone from a cDNA library prepared from etoposide-treated 3T3 cells. The remainder of the 2.4 Kb EI24 cDNA was isolated from a cDNA library prepared from untreated 3T3 cells, with the exception of the extreme 5'-end of the cDNA (non-coding region, see below) which was obtained by PCR methods. The DNA sequence of the composite 2118 bp EI24 cDNA is shown in FIG. 2. An open reading frame extends from nucleotide positions 84 to 1034, which codes for a 317 amino acid protein with a predicted molecular weight of 37 kD.

Comparison of the deduced sequence of the EI24 protein with the protein sequence database revealed homology to the 316 amino acid sequence CELF37C12.2 (accession number U00033) from C. elegans. A sequence alignment of the two proteins is shown in FIG. 3. EI24 and CELF37 exhibit 25% homology overall, and 36% identity across the most related region spanning amino acids 150 to 268. The CELF37 sequence was deduced by conceptual translation of *C. elegans* chromosome III DNA sequences (Wilson R., Ainscough R., Anderson K., Baynes C., Berks M., Bonfield J., Burton J., Connell M., Copsey T., Cooper J., Coulson A., Craxton M., Dear S., Du Z., Durbin R., Favello A., Fraser A., Fulton L., Gardner A., Green P., Hawkins T., Hillier L., Jier M., Johnston L., Jones M., Kershaw J., Kirsten J., Laisster N., Latreille P., Lightning J., Lloyd C., Mortimore B., O'Callaghan M., Parsons J., Percy C., Rifken L., Roopra A., Saunders D., Shownkeen R., Sims M., Smaldon N., Smith A., Smith M., Sonnhammer E., Staden R., Sulston J., Thierry-Mieg J., Thomas K., Vaudin M., Vaughan K., Waterston R., Watson A., Weinstock L., Wilkinson-Sproat J. and Wohldman P. (1994) *Nature*, 368, 32–38), and the function of this protein has not yet been determined. Neither EI24 nor CELF37 showed significant homology to any other proteins in the database.

Figure 4:
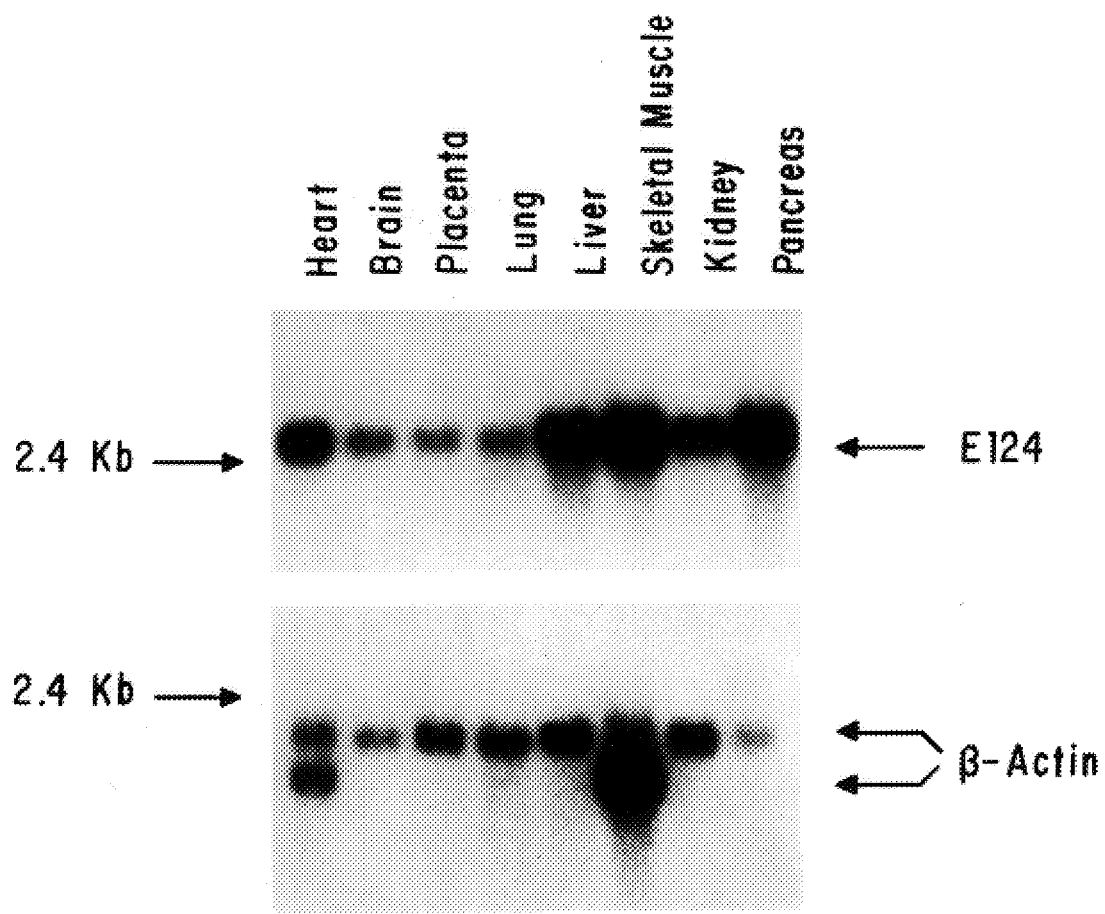
FIG. 4. Expression of the EI24 RNA in primary human tissues. A northern blot containing 2.0 $\mu$g of poly-A$^+$ RNA from the indicated tissues was probed with the entire coding region from the murine EI24 cDNA. The blot was stripped and rehybridized with a probe for b-actin as a loading control.

Comparison of the DNA sequence of EI24 with the nucleotide sequence database identified several human cDNA sequences that exhibited greater than 90% homology to the EI24 cDNA (Table I). These sequences, which appear to represent portions of the human EI24 homologue, were submitted to the database as partial cDNA's (EST clones) isolated from various human tissues. Neither the full cDNA sequence nor the function of this human homologue has been reported. These data suggested to the present inventors that the EI24 mRNA may be widely expressed in normal tissues. To examine the expression pattern of the human EI24 homologue, the murine EI24 cDNA was used to probe a northern blot containing mRNA from a variety of primary human tissues. A 2.5 kb mRNA was detected in all tissues examined (FIG. 4), indicating that the human EI24 homologue is expressed in diverse tissues.

TABLE I

Human cDNA sequences having greater than 90% homology to the EI24 cDNA.

| Accession Number | Description |
| --- | --- |
| gb/R17440 | yg14b04.r1 Homo sapiens cDNA clone |
| gb/T31497 | EST33594 Homo sapiens cDNA clone |
| gb/H85229 | yv85b08.r1 Homo spaiens cDNA clone |
| gb/T99735 | ye67e09.r1 Homo sapiens cDNA clone |
| emb/Z25927 | Homo sapiens partial cDNA clone |
| gb/N36667 | yx91d10.r1 Homo sapiens cDNA clone |
| gb/N35767 | yx81f05.r1 Homo sapiens cDNA clone |

Induction of the EI24 RNA requires p53.

Figure 5:
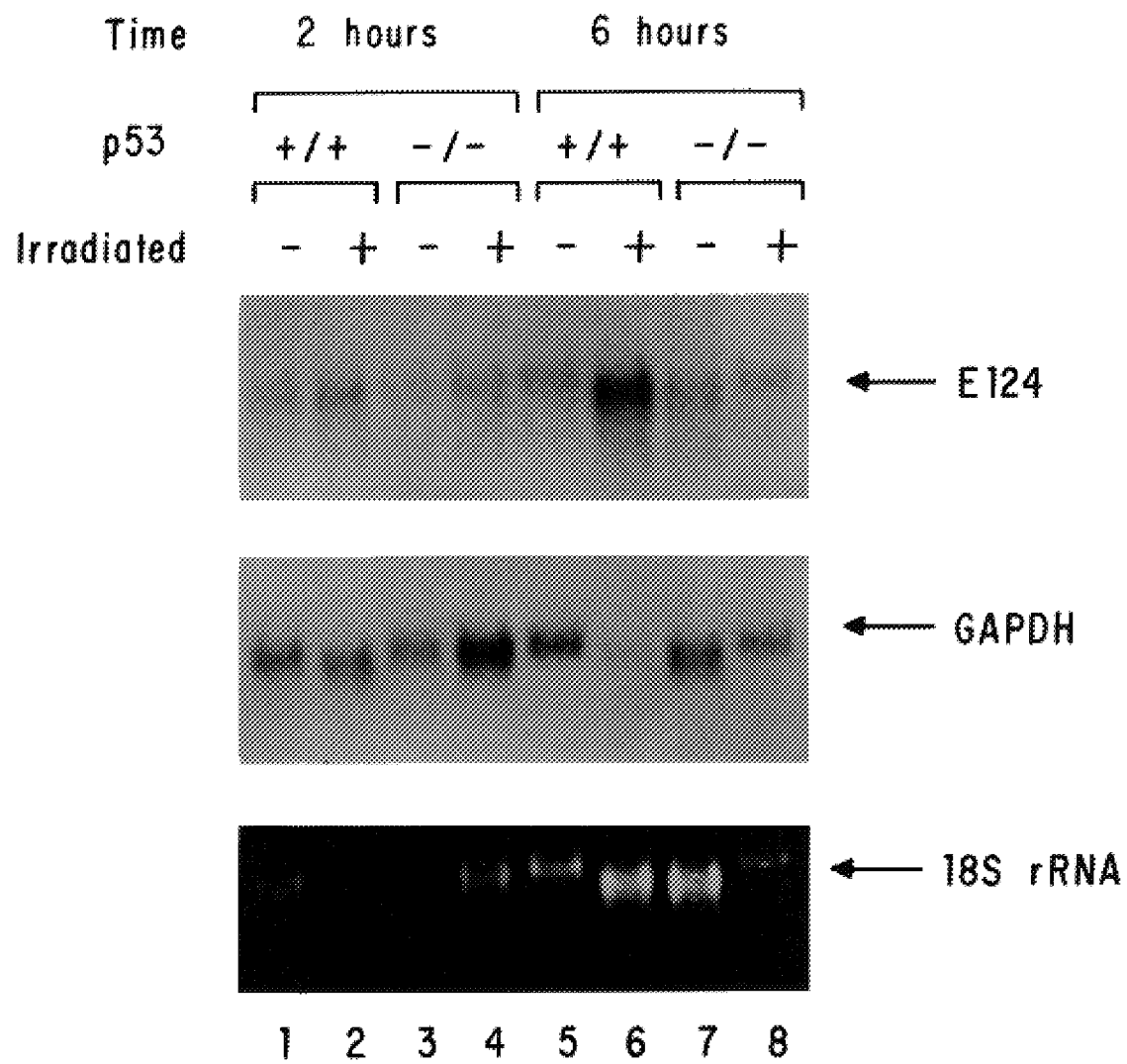
FIG. 5 Northern blot showing induction of EI24 RNA in irradiated thymocytes. Thymocytes isolated from wild-type (p53$^{+/+}$) or p53-deficient (p53$^{-/-}$) mice were left untreated, or irradiated, and total RNA was harvested after the times indicated. 10 $\mu$g of total RNA was loaded per lane, and the gel was stained with ethidium bromide to visualize the ribosomal RNA bands (18S rRNA shown). RNA was transferred to nitrocellulose, and the blot was hybridized with the EI24 cDNA. The blot was stripped and rehybridized with a probe for glyceraldehyde phosphate dehydrogenase (GAPDH) as a loading control.

To determine if the induction of EI24 is linked to a pathway regulated by p53, we examined its expression in cells lacking p53 function. p53 has been shown to play an essential role in thymocyte apoptosis in response to DNA damage (Clarke A. R., Purdie C. A., Harrison D. J., Morris R. G., Bird C. C., Hooper M. L. and Wyllie A. H. (1993) *Nature*, 362, 849–852; Lowe S. W., Schmitt E. M., Smith S. W., Osborne B. A. and Jacks T. (1993) *Nature*, 362, 847–849). We examined whether EI24 expression was induced in a p53-dependent manner in murine thymocytes exposed to ionizing radiation. Thymocytes derived from either wild-type or p53-deficient mice (see Materials and Methods) were treated with ionizing radiation and total RNA was isolated after 2 or 6 hours. The levels of EI24 expression were monitored by northern blot analysis (FIG. 5). While a low level of EI24 RNA was present in non-irradiated thymocytes from both wild-type and p53-null mice, there was a substantial induction of EI24 in wild-type, but not p53-deficient, tissue exposed to ionizing radiation. At 2 hours after treatment, there was about a 2-fold increase in RNA levels, and at 6 hours after treatment the RNA was induced at least 7-fold (FIG. 5, lane 6). These results are consistent with the pattern of EI24 expression in etoposide-treated 3T3 cells. It is noteworthy that when the northern blot was rehybridized with a GAPDH control probe, there was significantly lower signal in the wild-type 6-hours post irradiation sample; although the intensity of the 18S ribosomal RNA band in this sample was approximately the same as in the other lanes (FIG. 5, lane 6). Given that a significant fraction of the cells were dead or dying at this time point, we presume this reflects overall mRNA degradation during apoptosis. Thus, the induction of the EI24 gene seen in this sample may be an under-estimate. These results demonstrate that ionizing radiation induces EI24 in thymocytes in a p53-dependent manner. p53 is similarly required for etoposide induction of EI24 in transformed fibroblasts (see below).

EI24 mRNA is induced by over-expression of p53 in transformed fibroblasts.

Given that the EI24 mRNA was induced by two independent DNA-damaging agents thought to activate p53 (etoposide and ionizing radiation), we wondered whether elevation of p53 levels was sufficient to induce EI24 expression in p53-deficient cells. Murine embryonic fibroblasts (MEFs) obtained from a p53 "knockout" mouse (p53$^{-/-}$) or from a wild-type p53 mouse (p53$^{+/+}$), were transfected with adenovirus E1A and T24 H-ras (Lowe S. W., Jacks T., Housman D. E. and Ruley H. E. (1994) *Proc. Natl. Acad. Sci. USA*, 91, 2026–2030). The resulting cell lines were then treated with etoposide (50 $\mu$M) for 6 hours and northern blot analysis was performed as described above using poly-A$^+$ RNA (FIG. 6). No induction of EI24 was observed in etoposide-treated E1A/ras-transformed p53$^{-/-}$ cells, confirming that EI24 is induced by etoposide in a p53-dependent manner. The p53$^{+/+}$ cells expressed a 4-fold higher basal level of EI24 mRNA, even in the absence of etoposide treatment, which was further induced in response to etoposide. The high basal level of EI24 may reflect the action of wild-type p53 (see below) which is stabilized and present at higher levels in E1A/ras-transformed p53$^{+/+}$ cells than in their untransformed counterparts (Lowe S. W. and Ruley H. E. (1993) *Genes & Dev.*, 7, 535–545).

Figure 6:
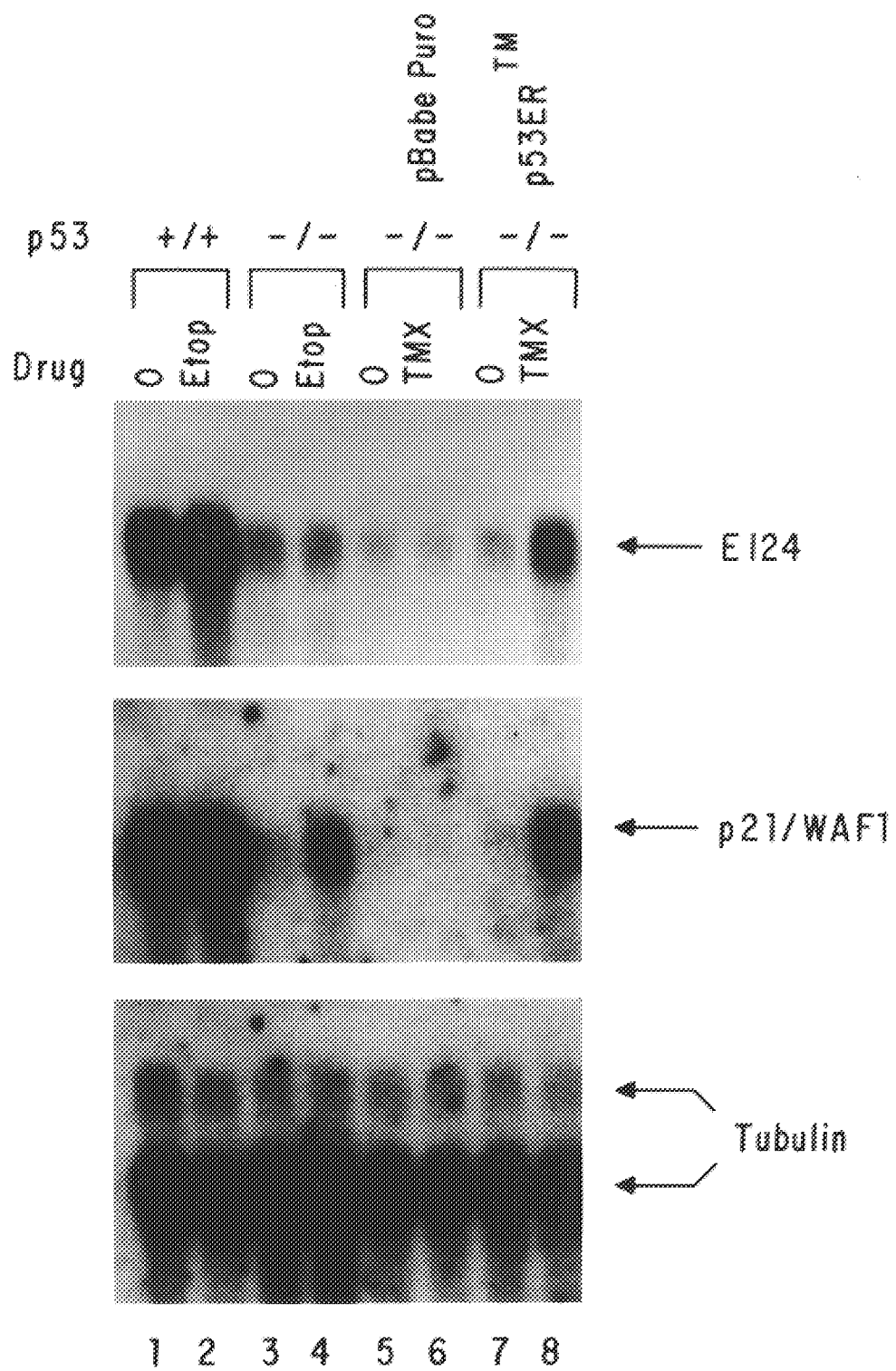
FIG. 6. Northern blot showing induction of EI24 RNA by p53 in EI A/ras transformed murine embryonic fibroblasts (MEFs). 1.0 $\mu$g of poly-A$^+$ RNA was loaded per lane. p53$^{+/+}$ and p53$^{-/-}$ MEFs were left untreated, or treated with 50 $\mu$M etoposide for 6 hours, as indicated (lanes 1–4). Alternately, p53$^{-/-}$ MEFs expressing either empty vector (pBabe Puro), or a tamoxifen-regulatable p53 (p53ER™) were left untreated, or treated with 3.3 μM tamoxifen (TMX) for 16 hours (lanes 5–8). The northern blot was hybridized sequentially with probes for EI24, p21/WAF1 and tubulin.

The p53$^{-/-}$ EIA/ras-transformed MEFs were then transfected with a p53-mutant estrogen receptor fusion protein (p53ER™). A similar p53-fusion, p53her, has been [Bdescribed previously and shown to be biologically active (Roemer K. and Friedmann T. (1993) *Proc. Natl. Acad. Sci. USA*, 90, 9252–9256). In the case of p53ER™, the ligand binding domain of the murine estrogen receptor has been mutated to permit selective activation by the estrogen receptor antagonist tamoxifen (Littlewood T. D., Hancock D. C., Danielian P. S., Parker M. G. and Evan G. I. (1995) *NAR*, 23, 1686–1690; Danielian P., White R., Hoare S., Fawell S. and Parker M. (1993) *Mol Endocrinol*, 7, 232–240). The p53ER™ fusion is constitutively expressed as an inactive species, and only acquires wild-type p53 function in the presence of tamoxifen (C. A. V. et al. submitted for publication). Activation of p53 by the addition of tamoxifen for 16 hours induced expression of the 2.4 kb EI24 mRNA in the p53ER™-transfected p53$^{-/-}$ cells, as detected by northern blot analysis (FIG. 6). No EI24 induction was observed upon addition of tamoxifen to a matched p53$^{-/-}$ control cell line (pBabe Puro) carrying the empty vector alone.

Activation of the p53ER™ fusion by tamoxifen was confirmed by re-hybridizing the northern blot with a probe for p21/WAF1, a gene known to be specifically induced by p53 (El-Deiry W. S., Tokino T., Velculescu V. E., Levy D. B., Parsons R., Trent J. M., Lin D., Mercer W. E., Kinzler K. W. and Vogelstein B. (1993) *Cell*, 75, 817–825). Like EI24, the WAF1 mRNA was strongly induced upon tamoxifen treatment in the p53ER™ p53$^{-/-}$ cells (FIG. 6, lanes 7 and 8), but not in the cells transfected with the empty vector pBabe Puro (FIG. 6, lanes 5 and 6). Additionally, the basal (no etoposide) levels of WAF1 mRNA, like that of EI24, were significantly elevated in E1A/ras transformed p53$^{+/+}$ cells (FIG. 6, lane 1), reflecting the high levels of endogenous p53 expressed in these cells. In this example, activation of p53, either by tamoxifen in the p53ER™-transfected cells, or by its stabilization in the EIA and ras-transformed p53$^{+/+}$ cells, resulted in induction of both EI24 and WAF1 mRNAs. These results demonstrate that activation of p53 is sufficient for induction of EI24, at least in the cell system described here.

Interestingly, the behavior of WAF1 RNA differed from that of EI24 RNA in the p53$^{-/-}$ MEFs which were treated with etoposide. While EI24 RNA was not induced by etoposide in these cells, WAF1 RNA was induced (see FIG. 6, lanes 3 and 4), although the maximal level of induction was lower than was seen in the p53$^{+/+}$ cells. Induction of WAF1 RNA through a p53-independent mechanism has been described previously (Macleod K. F., Sherry N., Hannon G., Beach D., Tokino T., Kinzler D., Vogelstein B. and Jacks T. (1995) *Genes & Dev.*, 9, 935–944; Michieli P., Chedid M., Lin D., Pierce J., Mercer W. and Givol D. (1994) *Cancer Res.*, 54, 3391–3395). The existence of a p53-independent pathway for apoptosis, triggered by etoposide (or irradiation), has also been described (Strasser A., Harris A. W., Jacks T. and Cory S. (1994) *Cell*, 79, 329–339) in p53$^{-/-}$ lymphoma cells, and in proliferating T cells derived from p53$^{-/-}$ mice.

Discussion

The cytotoxicity of etoposide, as well as other chemotherapeutic drugs, is dependent, at least in part, on its ability to trigger apoptosis through a p53-dependent pathway (Clarke A. R., Purdie C. A., Harrison D. J., Morris R. G., Bird C. C., Hooper M. L. and Wyllie A. H. (1993) *Nature*, 362, 849–852; Lowe S. W., Ruley H. E., Jacks T. and Housman D. E. (1993) *Cell*, 74, 957–967). Etoposide-induced apoptosis requires RNA synthesis (Walker P., Smith C., Youdale T., Leblanc J., Whitfield J. and Sikorska M. (1991) *Cancer Res.*, 51, 1078–1085), raising the possibility that one or more genes transactivated by p53 in response to etoposide is involved in implementing the cell death program. The EI24 gene, isolated and characterized in this study, is a candidate for a gene in this class based upon several properties of its expression. First, the EI24 mRNA is induced rapidly in response to etoposide exposure or ionizing radiation, with kinetics that precede or parallel the onset of apoptosis. Second, induction of EI24 mRNA in response to DNA damage was only observed in cells expressing functional p53. Finally, over-expression of p53, in the absence of etoposide or other DNA-damaging agents, results in induction of the EI24 gene.

The properties of EI24 expression are consistent with its potential role in p53-mediated apoptosis. The function of EI24 in apoptosis, may be restricted to a p53-dependent cell death pathway, since expression of EI24 mRNA was not altered following induction of apoptosis by either Fas ligation, or cytokine withdrawal in IL-3 dependent cells. EI24 is, therefore, not induced by apoptotic stimuli per se. EI24 may contribute to a different p53-dependent process, such as growth arrest or DNA repair.

Basal levels of EI24 expression appear independent of p53, while its induction in response to DNA damage is regulated by p53. p53 may transactivate EI24 either directly, by binding to sites within the EI24 promoter, or indirectly, by regulating the expression of a gene whose product in turn governs EI24 transcription.

The homology of the sequence of the EI24 protein to the *C. elegans* protein CELF37C12.2, implies an evolutionarily conserved function for EI24. There is substantial precedence for the structural and functional conservation in *C. elegans* and mammals of genes that regulate apoptosis (Steller H. (1995) *Science*, 267, 1445–1449). Examples include the *C. elegans* ced3 and ced9 cell death regulatory genes, whose mammalian counterparts, IL-1-β-converting enzyme (ICE) and bcl-2, respectively, modulate apoptosis in a similar fashion. The homology of EI24 to CELF37Cl2.2 raises the possibility that the regulation of EI24 will likewise be conserved. If so, the CELF37C12.2 gene may, by analogy to EI24, also be induced in *C. elegans* in response to DNA damage. This would suggest the existence of a conserved p53-like regulatory function in nematodes and provides a means to identify such genes.

Publications mentioned in this specification are indicative of the level of the skill of those skilled in the art to which this invention pertains. All publications are herein incorporated by reference, to the same extent as if each individual publication was specifically and individually indicated to be incorporated by reference.

While the invention has been described in connection with the specific embodiments thereof, it will be understood that it is capable of further modifications and this application is intended to cover any variations, uses, or adoptions of the invention following, in general, principles of the invention and including such departures from the present disclosure as come within known or customary practice within the art to which the invention pertains and as may be applied to the essential features hereinbefore set forth and as follows in the scope of the appended claims.

What is claimed is:

1. An isolated nucleotide sequence coding for EI24 protein obtained from the murine EI24 cDNA clone pKSEI24 cl 11 or the human EI24 cDNA clone pKSEI24 1–2.

2. The isolated nucleotide sequence of claim 1, wherein said sequence is as shown in FIG. 2 (SEQ ID NO:7).

3. The isolated nucleotide sequence of any one of claims 1 or 2, wherein said sequence comprises genomic DNA.

4. The isolated nucleotide sequence of any one of claims 1 or 2, wherein said sequence comprises cDNA.

5. The isolated nucleotide sequence of any one of claims 1 or 2, wherein said sequence comprise RNA.

6. An isolated recombinant DNA molecule consisting of a nucleotide sequence that codes for EI24 protein.

7. The isolated recombinant DNA molecule of claim 6, wherein said nucleotide sequence is as shown in FIG. 2 (SEQ ID NO.7).

8. The isolated recombinant DNA molecule of claim 7, wherein said molecule is a vector.

9. A vector consisting of a recombinant DNA molecule encoding EI24 protein, wherein said vector expresses a sequence that codes for EI24 protein in said recombinant DNA molecule.

10. A method for producing an isolated EI24 polypeptide, comprising:

(a) constructing the vector of claim 9;

(b) transforming a suitable host cell with said vector of Step (a), wherein said host cell is a mammalian cell;

(c) culturing said host cell under conditions which allow the expression of said EI24 polypeptide by said host cell; and (d) isolating said EI24 polypeptide expressed by said host cell of Step (c);

wherein said isolated EI24 polypeptide is produced.

11. The vector of claim 9, wherein said recombinant DNA molecule consists of a nucleotide sequence as shown in FIG. 2 (SEQ ID NO:7).

12. A host cell transformed with the vector of any one of claims 9 or 11, wherein said host cell is a mammalian cell.

13. A vector comprising a recombinant DNA molecule encoding EI24 protein, wherein said vector expresses an antisense RNA of said recombinant molecule.

14. A detectably labeled nucleotide probe, comprising a first nucleotide sequence which is complementary to a second nucleotide coding for EI24 protein obtained from the murine EI24 cDNA clone pKSEI24 cl. 11 and the human EI24 cDNA clone pKSEI24 1–2.

15. A method for detecting the expression of the EI24 gene in a biological sample comprising the step of identifying the presence of mRNA encoding EI24 protein obtained from the murine EI24 cDNA clone pKSEI24 cl 11 or the human EI24 cDNA clone pKSEI24 1–2, wherein the expression of the EI24 gene is detected.

16. The method according to claim 15 wherein the method for identifying said mRNA is Northern blotting.

17. A method of identifying an EI24 mRNA comprising the steps of:

(a) obtaining a cell sample;

(b) obtaining mRNA from the cell sample;

(c) performing a polymerase chain reaction on said mRNA using a primer corresponding to the unique regions of EI24 cDNA human or murine clone; and (d) detecting the presence of the products of the polymerase chain reaction, wherein said EI24 mRNA is identified.

18. A cDNA clone sesected from the group consisting of pKSEI24 cl. 11 pKSEI24 1–2.

* * * * *

UNITED STATES PATENT AND TRADEMARK OFFICE
CERTIFICATE OF CORRECTION

PATENT NO. : 5,843,659
DATED : December 1, 1998
INVENTOR(S) : Sophie M. Lehar and Braydon C. Guild It is certified that error appears in the above-identified patent and that said Letters Patent is hereby corrected as shown below:

Title page,
Item [56], line 3 of publications, "vol." should read -- Vol. --.

Item [57], Abstract,
Line 1, "EI24" should read -- *EI24* --;
Line 3, "EI24" should read -- *EI24* --;
Line 6, "EI24" should read -- *EI24* --;
Line 9, "EI24" should read -- *EI24* --;
Line 15, "EI24" should read -- *EI24* --;
Line 16, "EI24" should read -- *EI24* --;

Column 1,
Line 1, insert -- NOVEL -- before "APOPTOSIS", and "EI24" should read -- *EI24* --.
Line 9, first occurrence, "EI24" should read -- *EI24* --;

Column 2,
Line 6, after "10644", insert -- ) --;
Line 6, "bcl-2" should read -- *bcl-2* --;
Line 7, "bax" should read -- *bax* --;
Line 19, after "(1994)" insert -- . --;
Line 30, after "Gougeon" insert -- , --;
Line 40, delete "which";
Line 44, "gadd45, cyclin G, p21/WAF" should read -- *gadd45, cyclin G, p21/WAF* --;
Line 45, "bax" should read -- *bax* --;
Line 52, "e.g," should read -- *e.g.,* --;
Line 60, "EI24" should read -- *EI24* --;
Line 63, "EI24" should read -- *EI24* --;

Column 3,
Line 1, "EI24" should read -- *EI24* --; and "ras" should read -- *ras* --;
Line 2, "EI24" should read -- *EI24* --;
Line 19, "EI24" should read -- *EI24* --;
Line 24, "EI24" should read -- *EI24* --;
Line 36, "EI24" should read -- *EI24* --;

Column 4,
Line 7, after "by", insert -- , --;
Line 14, "EI24" should read -- *EI24* --;
Line 22, "EI24" should read -- *EI24* --;
Line 24, "EI24" should read -- *EI24* --;

UNITED STATES PATENT AND TRADEMARK OFFICE
CERTIFICATE OF CORRECTION

PATENT NO. : 5,843,659
DATED : December 1, 1998
INVENTOR(S) : Sophie M. Lehar and Braydon C. Guild Page 2 of 7

It is certified that error appears in the above-identified patent and that said Letters Patent is hereby corrected as shown below:

Column 4 (cont'd.),
Line 31, "μm" should read -- μM --;
Line 35, "EI24" should read -- *EI24* --;
Line 42, "EI24" should read -- *EI24* --;
Line 45, "EI24" should read -- *EI24* --;
Line 48, "EI24" should read -- *EI24* --;
Line 50, "EI24" should read -- *EI24* --;
Line 58, "EI24" should read -- *EI24* --;
Line 61, "EI24" should read -- *EI24* --;
Line 62, "EI A/ras" should read -- *EI A/ras* --;

Column 5,
Line 3, "EI24" should read -- *EI24* --; and "WAF1" should read -- *WAF1* --;
Line 5, "EI24" should read -- *EI24* --;
Line 19, "EI24" should read -- *EI24* --;
Line 38, "EI24" should read -- *EI24* --;
Line 62, after "supra" insert -- ) --;
Line 65, "in vitro" should read -- *in vitro* --;
Line 67, after "example" insert -- , --;

Column 6,
Line 30, "in vitro" should read -- *in vitro* --;

Column 8,
Line 23, "EI24" should read -- *EI24* --;
Line 24, "EI24" should read -- *EI24* --;
Line 37, after "encode" insert -- . --;
Line 67, Bacillus, Streptomyces, Pseudomonas, Salmonella" should read
-- *Bacillus, Streptomyces, Pseudomonas, Salmonella* --;

Column 9,
Line 1, "Serratia" should read -- *Serratia* --;
Line 3, "*species*" should read -- *species* --;
Line 10, Pseudomonas, Streptomyces" should read -- *Pseudomonas, Streptomyces* --;
Line 15, "int" should read -- *int* --;
Line 16, "bla" should read -- *bla* --;
Line 20, "trp" should read -- *tri* --;
Line 21, "recA, IacZ, IacI, and gal" should read -- *recA, IacZ, IacI, and gal* --;
Line 25, "Bacillus" should read -- *Bacillus* --;

UNITED STATES PATENT AND TRADEMARK OFFICE
CERTIFICATE OF CORRECTION

PATENT NO. : 5,843,659
DATED : December 1, 1998
INVENTOR(S) : Sophie M. Lehar and Braydon C. Guild It is certified that error appears in the above-identified patent and that said Letters Patent is hereby corrected as shown below:

Column 9 contd.
Line 27, "Streptomyces" should read -- *Streptomyces* --;
Line 39, "in vitro" should read -- *in vitro* --;

Column 10,
Line 2, "gal4" should read -- *gal4* --;

Column 11,
Line 4, "de novo" should read -- *de novo* --;

Column 12,
Line 23, "EI24" should read -- *EI24* --;
Line 24, "EI24" should read -- *EI24* --;
Line 30, "EI24" should read -- *EI24* --;
Line 32, "EI24" should read -- *EI24* --;
Line 34, "EI24" should read -- *EI24* --;

Column 13,
Line 22, "in vo" should read -- *in vivo* --;
Line 50, after "1981" delete one occurrence of " )";
Line 53, after "(1980)" insert -- ) --;

Column 14,
Line 61, "in vitro" or in vivo" should read -- *in vitro or in vivo* --;
Line 15, "in vivo" should read -- *in vivo* --;

Column 17,
Line 1, "In vivo" should read -- *In vivo* --;
Line 10, "very" should read -- vary --;
Line 19, "in vivo" should read -- *in vivo* --;
Lines 26-27, "in vivo" should read -- *in vivo* --;
Line 31, "in vivo" should read -- *in vivo* --;
Line 35, "in vivo" should read -- *in vivo* --;
Line 41, "racetic" should read -- raacetic --;
Line 46, "in vivo" should read -- *in vivo* --;
Line 67, "in" should read -- *in* --;

Column 18,
Line 1, "vivo" should read -- *vivo* --;
Line 14, "TGF-1" should read -- IGF-1 --;

UNITED STATES PATENT AND TRADEMARK OFFICE
CERTIFICATE OF CORRECTION

PATENT NO. : 5,843,659
DATED : December 1, 1998
INVENTOR(S) : Sophie M. Lehar and Braydon C. Guild It is certified that error appears in the above-identified patent and that said Letters Patent is hereby corrected as shown below:

Column 19,
Line 14, "or" should read -- of --;
Line 26, delete "in Section IV,";
Line 39, "EI24" should read -- *EI24* --;
Line 61, "AIDs" should read -- AIDS --;
Line 62, "AIDs" should read -- AIDS --;

Column 20,
Line 6, "in vivo" should read -- *in vivo* --;
Line 12, "in" should read -- by --;
Line 39, "agent" should read -- agents --;

Column 23,
Line 4, after "detergent" insert -- or --;
Line 44, "EI24" should read -- *EI24* --;
Line 48, "(dT cellulose) should read -- (dT) cellulose --;

Column 24,
Line 27, "EI24" should read -- *EI24* --;

Column 27,
Line 18, "inter alia" should read -- *inter alia* --;
Line 34, "EI24" should read -- *EI24* --;
Line 35, "EI24" should read -- *EI24* --;

Column 28,
Line 36, "EI24" should read -- *EI24* --;
Line 41, "EI24" should read -- *EI24* --;
Line 44, "EI24" should read -- *EI24* --;
Line 51, "4" should read -- 3 --;
Line 66, "EI24" should read -- *EI24* --;

Column 29,
Line 1, "EI24" should read -- *EI24* --;
Line 2, "EI24" should read -- *EI24* --;
Lines 6-12, adjust nucleotide sequence printing into column 30;
Line 14, "Ei24" should read -- *EI24* --;
Lines 17, both occurrences, "EI24" should read -- *EI24* --;
Line 19, "EI24" should read -- *EI24* --;
Line 22, "EI24" should read -- *EI24* --;

UNITED STATES PATENT AND TRADEMARK OFFICE
CERTIFICATE OF CORRECTION

PATENT NO. : 5,843,659
DATED : December 1, 1998
INVENTOR(S) : Sophie M. Lehar and Braydon C. Guild It is certified that error appears in the above-identified patent and that said Letters Patent is hereby corrected as shown below:

Column 29 contd.
Line 45, "EI24" should read -- $EI24$ --;
Line 49, "E1A and ras" should read -- $E1A$ and $ras$ --;
Line 51, "E1A" should read -- $E1A$ --;
Line 52, "H-ras" should read -- $H$-$ras$ --;
Line 61, "p53" should read -- $p53$ --;

Column 30,
Line 49, "EI24" should read -- $EI24$ --; and "Etoposide" should read -- etoposide --;
Line 50, "Induced" should read -- induced -- and "MRNA" should read -- mRNA --;
line 51, "EI24" should read -- $EI24$ -- and "CDNA" should read -- cDNA --;
Line 54, "EI24" should read -- $EI24$ --;
Line 56, "EI24" should read -- $EI24$ --;
Line 60, "EI24" should read -- $EI24$ --;
Line 67, "C. elegans" should read -- $C.\ elegans$ --;

Column 31,
Line 20, "EI24" should read -- $EI24$ --;
Line 23, "EI24" should read -- $EI24$ --;
Line 24, "EI24" should read -- $EI24$ --;
Line 29, "EI24" should read -- $EI24$ --;
Line 31, both occurrences; "EI24" should read -- $EI24$ --;
Line 34, "EI24" should read -- $EI24$ --;
Line 40, "EI24" should read -- $EI24$ --;
Line 49, "EI24" should read -- $EI24$ --;
Line 50, "EI24" should read -- $EI24$ --;
Line 59, "EI24" should read -- $EI24$ --;
Line 64, "EI24" should read -- $EI24$ --;
Line 66, "EI24" should read -- $EI24$ --;

Column 32,
Line 1, "EI24" should read -- $EI24$ --;
Line 15, "EI24" should read -- $EI24$ --;
Line 17, "EI24" should read -- $EI24$ --;
Line 19, "EI24" should read -- $EI24$ --;
Line 21, "EI24" should read -- $EI24$ --;
Line 23, "EI24" should read -- $EI24$ --;
Line 26, "EI24" should read -- $EI24$ --;
Line 30, "E1A" should read -- $E1A$ -- and "H-ras" should read -- $H$-$ras$ --;
Line 35, "EI24" should read -- $EI24$ --;

UNITED STATES PATENT AND TRADEMARK OFFICE
CERTIFICATE OF CORRECTION

PATENT NO. : 5,843,659
DATED : December 1, 1998
INVENTOR(S) : Sophie M. Lehar and Braydon C. Guild It is certified that error appears in the above-identified patent and that said Letters Patent is hereby corrected as shown below:

Column 32 contd.
Line 39, "EI24" should read -- *EI24* --;
Line 41, "EI24" should read -- *EI24* --;
Line 43, "E1A/ras" should read -- *E1A/ras* --;
Line 46, "E1A/ras" should read -- *E1A/ras* --;
Line 49, "Bdescribed" should read -- described --;
Line 62, "EI24" should read -- *EI24* --;
Line 64, "EI24" should read -- *EI24* --;

Column 33,
Line 3, "WAF1" should read -- *WAF1* --;
Line 6, "EI24" should read -- *EI24* --;
Line 7, "WAF1" should read -- *WAF1* --;
Line 11, "WAF1" should read -- *WAF1* -- and "EI24" should read -- *EI24* --;
Line 12, "E1A/ras" should read -- *E1A/ras* --;
Line 16, "E1A and ras" should read -- *E1A and ras* --;
Line 17, EI24 and WAF1" should read -- *EI24 and WAF1* --;
Line 19, "EI24" should read -- *EI24* --;
Line 20, "WAF1" should read -- *WAF1* --;
Line 21, "EI24" should read -- *EI24* --;
Line 22, "EI24" should read -- *EI24* --;
Line 23, "WAF1" should read -- *WAF1* --;
Line 26, "WAF1" should read -- *WAF1* --;
Line 50, "EI24" should read -- *EI24* --;
Line 52, "EI24" should read -- *EI24* --;

Column 34,
Line 2, "EI24" should read -- *EI24* --;
Line 6, "EI24" should read -- *EI24* --;
Line 7, "EI24" should read -- *EI24* --;
Line 9, "EI24" should read -- *EI24* --;
Line 10, "EI24" should read -- *EI24* --;
Line 13, "EI24" should read -- *EI24* --; and "per se" should read -- *per se* --;
Line 14, "EI24" should read -- *EI24* --;
Line 16, "EI24" should read -- *EI24* --;
Line 18, "EI24" should read -- *EI24* --;
line 19, "EI24" should read -- *EI24* --;
Line 21, "EI24" should read -- *EI24* --;
Line 28, "ced3 and ced9" should -- *ced3* and *ced9* --;

UNITED STATES PATENT AND TRADEMARK OFFICE
CERTIFICATE OF CORRECTION

PATENT NO. : 5,843,659
DATED : December 1, 1998
INVENTOR(S) : Sophie M. Lehar and Braydon C. Guild It is certified that error appears in the above-identified patent and that said Letters Patent is hereby corrected as shown below:

Column 34, contd.
Line 30, "bcl-2" should read -- *bcl-2* --;
Line 32, "EI24" should read -- *EI24* --;
Line 34, "EI24" should read -- *EI24* --;

Column 49,
Line 28, "EI24" should read -- *EI24* --;
Line 29, "EI24" should read -- *EI24* --;

Column 50,
Line 37, "EI24" should read -- *EI24* -- and "and" should read -- or --;
Line 38, "EI24" should read -- *EI24* --;
Line 39, "EI24" should read -- *EI24* --;
Line 42, "EI24" should read -- *EI24* --;
Line 43, "EI24" should read -- *EI24* --;
Line 44, "EI24" should read -- *EI24* --;
Line 47, "EI24" should read -- *EI24* --;
Line 53, "EI24" should read -- *EI24* --;
Line 55, "EI24" should read -- *EI24* --;
Line 57, "sesected" should read -- selected --.

Signed and Sealed this

Thirtieth Day of October, 2001

Attest:

*Attesting Officer*

NICHOLAS P. GODICI
*Acting Director of the United States Patent and Trademark Office*